United States Patent
Pollard

(10) Patent No.: US 9,511,083 B2
(45) Date of Patent: Dec. 6, 2016

(54) CARDIAC GLYCOSIDES TO TREAT CYSTIC FIBROSIS AND OTHER IL-8 DEPENDENT DISORDERS

(71) Applicant: Bette Pollard, Potomac, MD (US)

(72) Inventor: Bette Pollard, Potomac, MD (US)

(*) Notice: Subject to any disclaimer, the term of this patent is extended or adjusted under 35 U.S.C. 154(b) by 0 days.

(21) Appl. No.: 14/040,392

(22) Filed: Sep. 27, 2013

(65) Prior Publication Data

US 2014/0187505 A1 Jul. 3, 2014

Related U.S. Application Data

(63) Continuation of application No. 12/229,399, filed on Nov. 12, 2009, now Pat. No. 8,569,248, which is a continuation of application No. 10/515,260, filed as application No. PCT/US03/16733 on May 28, 2003.

(60) Provisional application No. 60/383,117, filed on May 28, 2002.

(51) Int. Cl.
*A61K 31/704* (2006.01)
*A61K 31/7048* (2006.01)

(52) U.S. Cl.
CPC ......... *A61K 31/704* (2013.01); *A61K 31/7048* (2013.01)

(58) Field of Classification Search
USPC .......................................... 514/26
See application file for complete search history.

(56) References Cited

U.S. PATENT DOCUMENTS 5,545,623 A * 8/1996 Matsumori ............ 514/26
6,380,167 B1 * 4/2002 Braude ............... 514/26

FOREIGN PATENT DOCUMENTS

WO WO9728808 * 8/1997 ........... A61K 31/705

OTHER PUBLICATIONS

Ammirante et al., "B-cell-derived lymphotoxin promotes castration-resistant prostate cancer." Nature 2010:464;302-306.*
Yeh et al., "Inhibitory effects of digitalis on the proliferation of adrogen dependent and independent prostate cancer cells." The Journal of Urology, vol. 166, pp. 1937-1942, Nov. 2001.*
Inoue et al., "Interleukin 8 Expression Regulates Tumorigenicity and Metastases in Androgen-independent Prostate Cancer." Clinical Cancer Research: vol. 6, pp. 2104-2119, May 2000.*
Ozen et al., "Widespread deregulation of microRNA expression in human prostate cancer." Oncogene (2008) 27, 1788-1793.*
Haustein et al, "Studies on cardioactive steroids IV Influence of nitrate ester on cardiac and extracardiac activity," Pharmacology 20:15-20, 1980.
Kulikov et al, "Ouabain activates signaling pathways associated with cell death in human neuroblastoma," 1768(7), pp. 1691 to 1702, Biochim. Biophys. Acta, Jul. 2007.
Qiu et al, "Proteomics investigation of protein expression changes in ouabain induced apoptosis in human umbilical vein endothelial cells," J. Cell. Biochem. 104(3), pp. 1054-1064, Jun. 1, 2008.
Qiu et al, "Comparative proteomics analysis reveals role of heat shock protein 60 in digoxin-induced toxicity in human endothelial cells," Biochimica et Biophysica Acta 1784 (2008) 1857-1864.
Yang et al, "Digitoxin induces apoptosis in cancer cells by inhibiting nuclear factor of activated T-cells-driven c-MYC expression," Journal of Carcinogenesis 12(8) 2013.

* cited by examiner

*Primary Examiner* — Walter Webb
(74) *Attorney, Agent, or Firm* — Walter Ottesen, P.A.

(57) ABSTRACT

Disclosed is the use of a cardiac glycoside to decrease or inhibit the secretion of proinflammatory mediators in the treatment of disease conditions characterized by elevated levels of the proinflammatory mediator. The cardiac glycoside is administered to a mammalian subject in need of such treatment, and dosage is adjusted to the mass of the recipient and the need of the recipient to reduce or inhibit the level of the proinflammatory mediator. The proinflammatory mediators suppressed by the invention include IL-8, IL-6, TNFalpha, ICAM-1, IFNgamma, IL-1-beta, MCP-1, MIP-2, and/or epithelial-mesenchymal-transition (EMT). The cardiac glycoside, digitoxin or oleandrin, can be formulated for administration by injection or as an aerosol administered to the respiratory tract or by being ingested, or as nose drops or nasal spray. According to one use, the digitoxin controls microRNA expression in castration-resistant prostate cancer. The microRNA suppresses IL-8 and IL-6 expression in these cells.

16 Claims, 11 Drawing Sheets

(I) Oleandrin IC$_{50}$ = 2.0 nM (II) Digitoxin IC$_{50}$ = 0.9 nM (III) Digoxin IC$_{50}$ = 27 nM (IV) Ouabain
$IC_{50} = 7.9$ nM (V) Digoxigenin
$IC_{50} = 34$ nM (VI) Digitoxigenin
$IC_{50} = 74$ nM (VII) Acetyl-Strophanthidin
$IC_{50} = 117$ nM (VIII) Digoxigenin, 3,12-diAc Vehicle Control
INFLAMATION Digitoxin, 0.03 mg/.kg

CARDIAC GLYCOSIDES TO TREAT CYSTIC FIBROSIS AND OTHER IL-8 DEPENDENT DISORDERS

This application claims priority from U.S. patent application Ser. No. 12/229,399, filed Nov. 12, 2009, which is a continuation of U.S. patent application Ser. No. 10/515,260, filed Aug. 26, 2005, which is a national stage entry of PCT/US03/16733, filed May 28, 2003, which claims the benefit of U.S. Provisional Patent Application Ser. No. 60/383,117, filed May 28, 2002. The entireties of these applications are incorporated herein by reference.

FIELD OF THE INVENTION

The present invention relates generally to the use of cardiac glycosides to decrease or inhibit IL-8 secretion. The present invention further relates to the use of cardiac glycosides to decrease or inhibit inflammation.

The present invention relates generally to the use of cardiac glycosides to decrease or inhibit IL-8, IL-6, and other immune system secretions. More particularly, the invention relates to a method of treating a patient in need of treatment for a disease condition caused or aggravated by an excessive level of IL-8, comprising administering a cardiac glycoside that lacks an oxygen-containing substituent at both C11 and C12 and has glycosyl moieties at the C3 position, wherein the cardiac glycoside is administered at a concentration of from about 1 nM to about 2 nM, but tested in the examples mentioned herein at 4.7 nM to 47 nM, adjusted to the mass of the recipient and the need of the recipient to inhibit or reduce the level of IL-8. The present invention further relates to the use of cardiac glycosides to decrease or inhibit inflammation and thereby treat a disease (s) or problem to the mammal or human.

BACKGROUND OF THE INVENTION

Inflammation is a complex response to localized injury or other trauma which involves various immune-system cells and numerous mediators. Interleukin-8 (IL-8, CXCL8) and Interleukin-6 (IL-6) are some of the major mediators of the inflammatory response. They are chemokines and cytokines secreted by macrophages, endothelial cells, monocytes, fibroblasts and neutrophils and are chemotactic for neutrophils, basophils and T cells, inducing neutrophil adherence to vascular endothelium and extravasation into tissues. IL-8, IL-6 and other immune cells are activated by cis-acting transcription factors such as NFKB. The NFKB signaling cascade is hypothesized to be initiated by several independent pathways involving receptors for TNF-a, IL-1, and bacterial lipopolysaccharides (LPS), which then converge on NIK, or on members of the MAP6K family. (Eidelman et al., 2001) IL-8 and IL-6 secretion is increased by oxidant stress and can also induce oxidant stress mediators. Elevated IL-8 and IL-6 levels can therefore play a damaging role as well as aid in the healing process.

Individuals with cystic fibrosis (CF) have elevated levels of IL-8. As the cystic fibrosis patient ages, the cystic fibrosis lung becomes characterized by elevated levels of white cells including polymorphonuclear leukocytes, macrophages, monocytes, lymphocytes and eosinophils. It is hypothesized that these cells are attracted from the circulation into the airway by the high levels of IL-8 and other pro-inflammatory factors such as IL-113, IL-6, leukotriene B4, RANTES, and TNFa. These factors mark the character of the cystic fibrosis lumenal milieu (Bonfield, et al. (1995a); ibid (1995b)). Among these factors, IL-8 ranks as the most prevalent and potent. IL-8 is of specific importance for cystic fibrosis because it is profoundly elevated in bronchoalveolar lavage fluids, sputum, and serum from cystic fibrosis patients (Dean, et al. (1993); Richman-Eisenstat, et al. (1993); Francoeur. et al. (1995); Armstrong, et al. (1997)). IL-8 protein is elevated in bronchoalveolar lavage fluids from infants with cystic fibrosis as early as 4 weeks of age (Khan, et al. (1995)). Hypersecretion of IL-8 occurs prior to objective evidence of infection by viruses, fungi or common cystic fibrosis pathogenic bacteria (Khan, et al (1995)). The concept of the generality of a pro-inflammatory state for cystic fibrosis epithelia is further manifest by the fact that fecal IL-8 levels in cystic fibrosis children are approximately 1000-fold elevated over non-cystic fibrosis controls (Briars, et al. (1995)). Fecal IL-8 levels correlate with lung function (FEV1, forced expiratory volume in one second), and to some extent with established *Pseudomonas* infection. A study with bronchial biopsies from cystic fibrosis patients undergoing lung transplant has demonstrated consistent up-regulation of IL-8 expression in submucosal gland cells (Tabary et al. (1998)).

It would therefore be desirable to develop compositions that reduce excessive inflammation, particularly compositions that reduce the secretion of IL-8 and other pro-inflammatory cytokines from cells secreting elevated levels of these compounds. These compositions could be useful in the treatment of disease conditions characterized by elevated levels of inflammatory cytokines.

SUMMARY OF THE INVENTION

The invention comprises compositions and methods for reducing or inhibiting inflammation. Specifically, provided herein are compositions and methods for inhibiting the secretion of IL-8, IL-6 and other cytokines and chemokines and other overly-abundant immune system response material from a cell secreting elevated levels of these. Such methods comprise administering to a mammalian subject in need of such treatment or prevention a composition comprising effective amounts of one or more cardiac glycosides alone or in combination with other anti-inflammatory or therapeutic agents.

The present invention discloses the use of digitoxin as an example cardiac glycoside useful in suppressing IL-8 and other proinflammatory cytokines and chemokines, which includes but are not limited to IL-6, TNFalpha, ICAM-1, in cystic fibrosis cells (Table 10). The invention also discloses the use of cardiac glycosides, including but not limited to digitoxin dependent suppression of IL-8 and IL-6, in the context of digitoxin dependent suppression of castration resistant prostate cancer (Tables 4, 5, and 6). Concomitantly, digitoxin suppresses the epithelial-mesenchimal-transition (EMT) in rodent and human prostate cancer cells (Tables 8 and 9, respectively), and significantly changes microRNA expression (Table 7) in these cells. The invention describes the reduction of IL-8 and related pro-inflammatory cytokines in a rodent model of influenza (FIG. 9). Herein also is described the reduction of rheumatoid arthritis by digitoxin in a rodent model (FIGS. 7 and 8). The identified microRNAs may also be used to treat the disease(s).

Cardiac glycosides are a class of naturally occurring drugs consisting of glycone and aglycone moieties. The aglycone moiety is a steroid nucleus with a unique fused ring system that makes the aglycone moiety structurally distinct from the other more common steroid ring systems. Rings A/B and C/D are cis-fused while rings B/C are trans-fused. Most cardiac glycosides have one to four sugars attached to the 3'-OH group. The sugars most commonly used include L-rhamnose, D-glucose, D-digitoxose, Ddigitalose, D-digginose, D-sarmentose, L-vallarose, and D-fructose. Exemplary cardiac glycosides include, but are not limited to, oleandrin, digitoxin, digoxin, ouabain, digoxigenen, digitoxigenen, and acetyl-stropanthidin, bufalin, proscilleridin, peruvoside, and their various foreseen and readily provided complexes, derivatives, salts, solvates, isomers, enantiomers, polymorphs, and prodrugs.

Previously published data have implicated a dysfunctional TNFa/NFkB signaling pathway as responsible for the pro-inflammatory phenotype of the CF lung (Eidelman et al, 2001a). To test whether this pathway might be a target for digitoxin, Reverse Phase Protein Microarrays were prepared from CF lung epithelial IB3-1 and CFTR-repaired IB3-1/S9 cells treated with Inhibitory Concentration (IC)-90 concentrations of all of the active cardiac glycosides. IC-90 means a concentration of drug that blocks 90% of IL-8 secretion from the IB3-1 cells. It was found that digitoxin and the other active species modestly suppressed phosphorylation of IKKalpha, but significantly suppressed constitutive phosphorylation of IkBalpha and NFkB, p65 (Srivastava et al *PNAS,* 2004). (See FIG. 1).

Within the methods and compositions of the invention, one or more cardiac glycosides alone or in combination with one or more other therapeutic agents as disclosed herein is/are effectively formulated or administered to treat or prevent inflammation or conditions caused or aggravated by inflammation. One or more of the cardiac glycosides alone or in combination with one or more other therapeutic agents as disclosed herein is/are effectively formulated or administered as an IL-8, IL-6 or other chemokines and cytokines inhibiting agent and/or a cellular protein binder or inhibitor effective for treating excessive production of IL-8 and/or related disorders. In exemplary embodiments, digitoxin is demonstrated for illustrative purposes to be an anti-inflammatory and/or IL-8 or other chemokine/cytokine inhibiting effective agent in pharmaceutical formulations and therapeutic methods, alone or in combination with one or more adjunctive therapeutic agent(s). The present disclosure further provides additional, pharmaceutically acceptable cardiac glycosides in the form of a native or synthetic compound, which are effective as anti-inflammatories and/inhibiting therapeutic agents within the methods and compositions of the invention.

Within additional aspects of the invention, combinatorial formulations and methods are provided which employ an effective amount of a cardiac glycoside in combination with one or more secondary or adjunctive active agent(s) that is/are combinatorially formulated or coordinately administered with the cardiac glycoside to yield an effective inhibitor of the inflammatory response and/or of excessive IL-8 production.

The invention achieves these objectives and satisfies additional objectives and advantages by providing surprisingly effective methods and compositions for decreasing and/or inhibiting inflammation, particularly by inhibiting IL-8 and other mediators production in cells that are producing an excessive amount. The present invention may be understood more fully by reference to the detailed description and examples, which are intended to exemplify non-limiting embodiments of the invention.

BRIEF DESCRIPTION OF THE DRAWINGS

The foregoing, as well as other objects and advantages of the invention, will become apparent from the following detailed description when taken in conjunction with the accompanying drawings, wherein like reference characters designate like parts throughout the several views, and wherein.

DETAILED DESCRIPTION OF THE PREFERRED EMBODIMENTS

The present invention teaches methods and compositions for preventing or treating elevated IL-8 levels in a mammalian subject, comprising administering to a patient in need of such treatment or prevention an effective amount of one or more cardiac glycosides alone or in combination with a secondary anti-inflammatory or other therapeutic agent.

IL-8 and/or inflammatory inhibiting formulations and methods provided herein employ a cardiac glycoside including all active and potent pharmaceutically acceptable compounds of this description as well as various foreseen and readily provided synthetically formulated cardiac glycosides with synthetic organic chemistry and combinations thereof with other adjunct therapies as well as with nanoparticles for delivery systems.

Within the formulations and methods of the invention, a cardiac glycoside alone or in combination with an additional therapeutic is effectively used to treat or prevent inflammation and conditions complicated by inflammation. A cardiac glycoside may be further used alone or in combination with an additional therapeutic to treat or prevent excessive IL-8, IL-6 or other inflammatory mediator production in mammals suffering from a condition complicated by or associated with excessive IL-8 production. Cardiac glycosides differ from one another, including their partition coefficients in octanol/water systems, as described in Table 1.

As described above, cystic fibrosis, as well as other conditions, is characterized by a high level of spontaneous, baseline IL-8 secretion. The mechanism of this high baseline secretion is not known, but may be associated with upregulation of a set of genes associated with the TNFaR/NFKB pathway (Eidelman. et al. (2001 a)).

Figure 3:
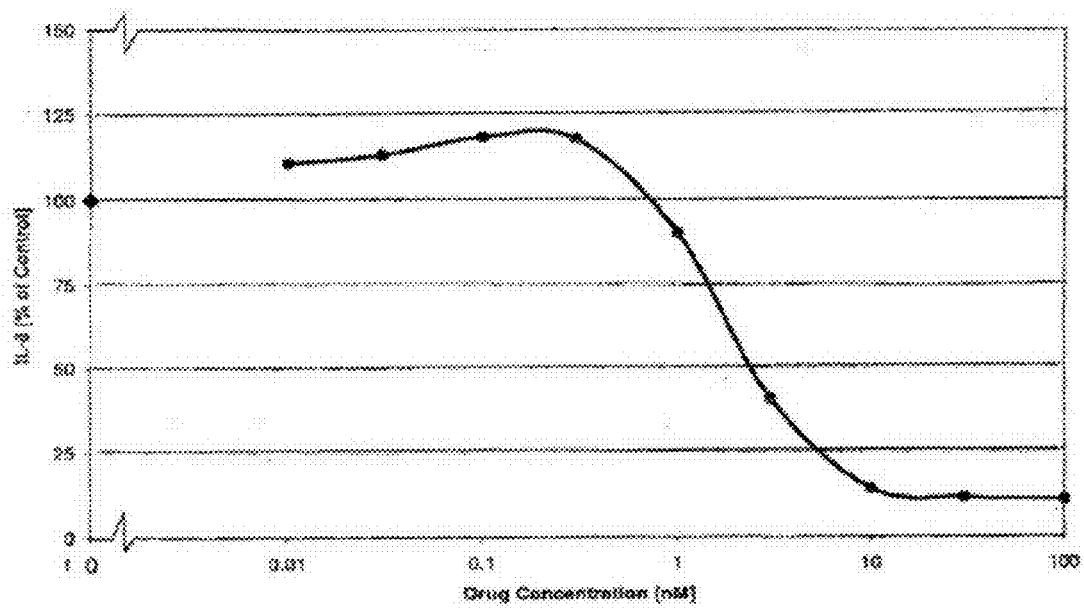
FIG. 3 is a graph showing the inhibitory effect of oleandrin on Baseline IL-8 secretion from cystic fibrosis lung epithelial cell IB-3. The inhibitory concentration (IC)-50 (concentration causing 50% inhibition) is ca. 2 nM (viz., $2 \times 10^{-9}$ M).
Figure 4A:
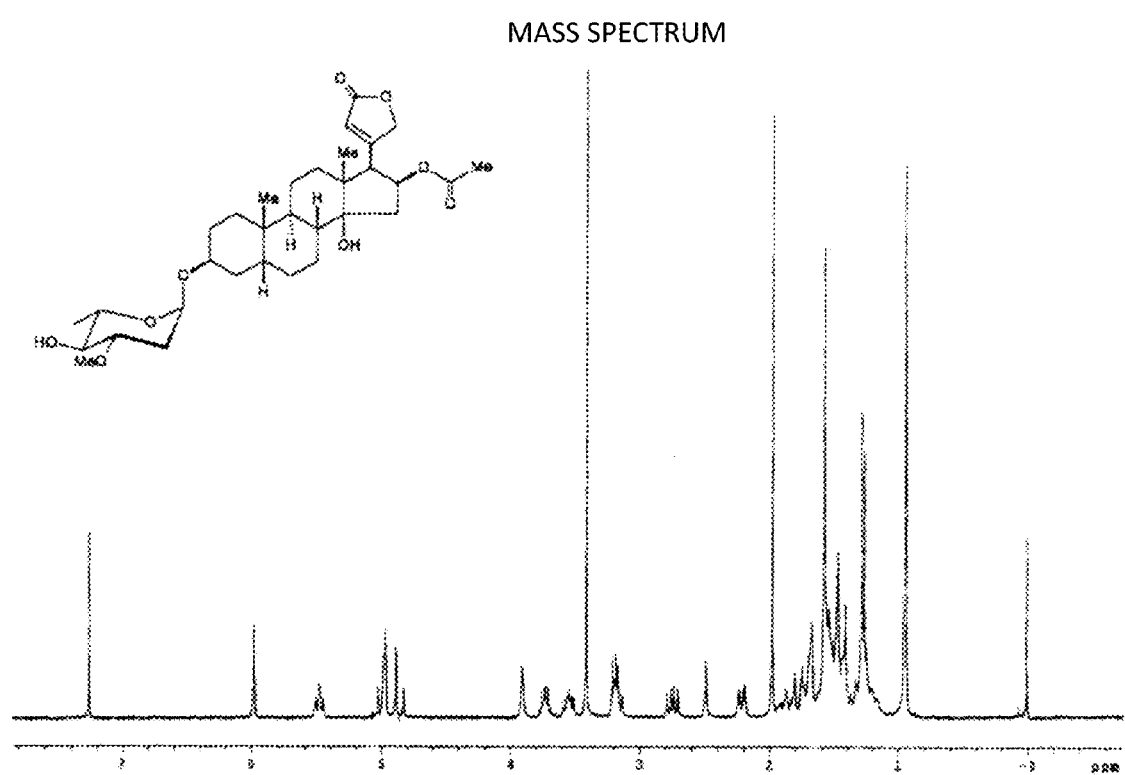
FIG. 4A illustrates the mass spectrum of oleandrin used in these experiments.
Figure 4B:
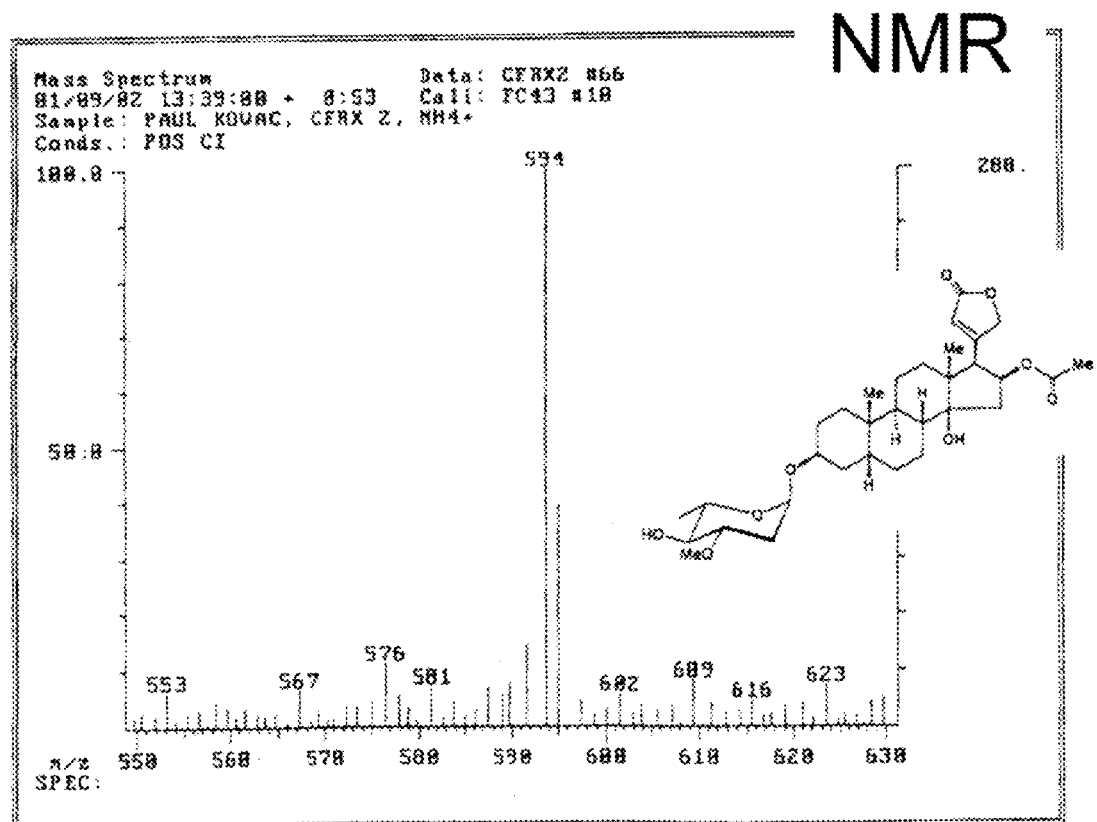
FIG. 4B illustrates the nuclear magnetic resonance (NMR) spectrum.
Figure 5A:
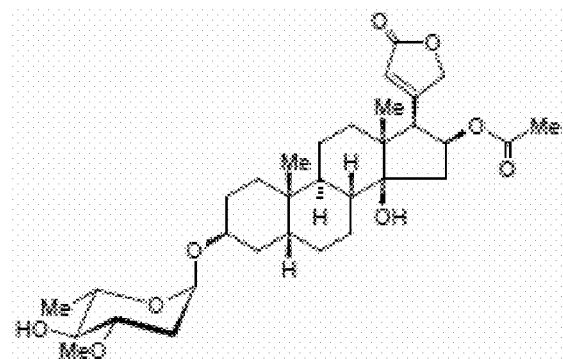
FIGS. 5A through 5H illustrate the structures of various oleandrin analogues.
Figure 5B:
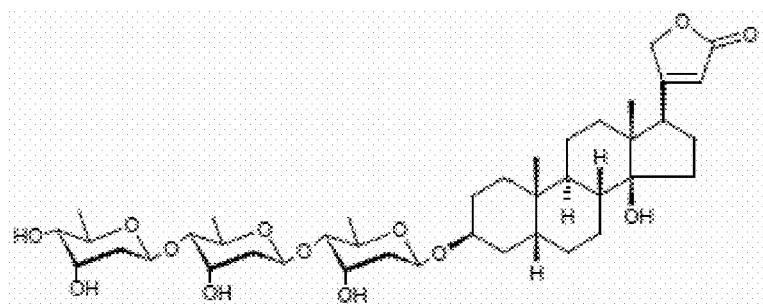
Figure 5C:
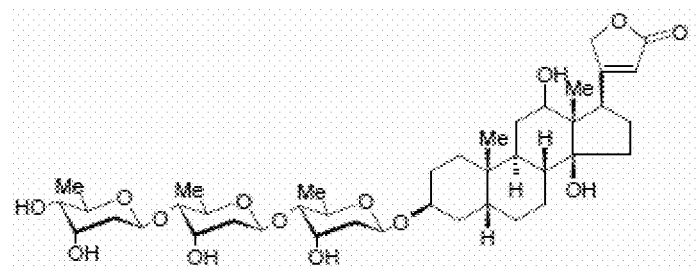
Figure 5D:
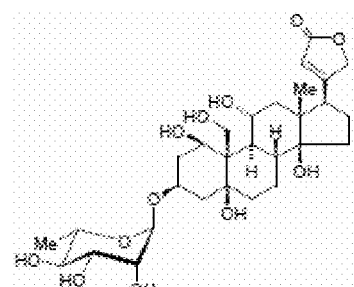
Figure 5E:
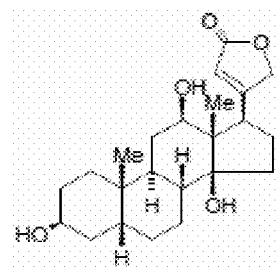
Figure 5F:
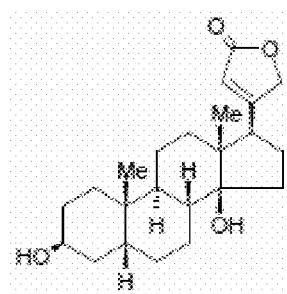
Figure 5G:
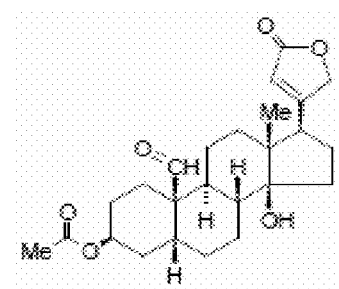
Figure 5H:
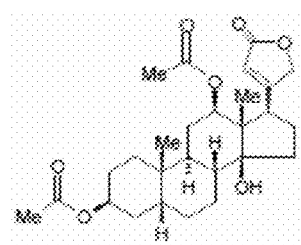

As described in Example 1 and Table 2, the cystic fibrosis lung epithelial cell line IB-3 was therefore exposed to different concentrations of oleandrin and various other cardiac glycosides over a 48 hour incubation period. Oleandrin was obtained from Indofine Chemicals, Hillsborough, N.J. FIGS. 4A and 4B show plots generated for the oleandrin used in these experiments by NMR and Mass Spectroscopy, respectively. IL-8 levels were measured using an ELISA kit (R& D Systems, Minneapolis, Minn.). The titration in FIG. 3 shows an IC50 (dose for 50% inhibition) for spontaneous IL-8 secretion of approximately 2 nM. The data plotted in FIG. 3 are the average of 3 separate experiments.

These experiments led to the determination of the structure-activity-relationship (SAR) for oleandrin suppression of IL-8 secretion from cystic fibrosis lung epithelial cell (See Table 3). Oleandrin and related cardiac glycosides are characterized by a cholesterol nucleus, the possible attachment of sugars at the position 3-OH position, an unsaturated lactone ring at the C-17 position, and various chiral substitutions throughout the structure. Experiments were conducted to elucidate the structure-activity-relation (SAR) by testing the potency of various modified versions of oleandrin. In this manner, the pharmacophor was specified.

Seven compounds were identified as cardiac glycoside variants of oleandrin and tested for activity. The data are given in Table 2, which illustrates the amount of cardiac glycoside drugs needed for 50% inhibition of release of IL-8 from cystic fibrosis lung epithelial cells. The most potent cardiac glycosides are digitoxin and oleandrin. The chemical structures of the compounds tested are shown in FIGS. 5A through 5H.

TABLE 1

Partition co-efficients in Octanol/water system.
LIPOPHILICITY OF CARDIAC GLYCOSIDES
Table 1 The partition coefficients (P) in octanol/water system, $R_{ot}$ values for the reversed-phase thin layer chromatography (mobile phase: methanol/water 30:70), retentions (K') for the reversed-phase high pressure liquid chromatography (eluent acetonitrile/water 45:55) and the $ID_{50}$ values of inhibitory effects of the cardiotonic steroids on the guinea-pig heart $Na^+$-$K^+$-ATPase

| | Cardenolides | P | $R_{ot}$ | K' | $ID_{50}$ ($\times 10^{-4}$ mol $l^{-1}$) |
|---|---|---|---|---|---|
| 1 | Digitoxigenin | 270.0 ± 94.1 | 1.03 | 1.81 | 1.63 ± 0.06 |
| 2 | Digitoxigenin-mono-digitoxoside | 320.0 ± 56.5 | 1.09 | 1.89 | 0.54 ± 0.03 |
| 3 | Digitoxigenin-bis-digitoxoside | 580.0 ± 84.6 | 1.28 | 2.39 | 0.50 ± 0.03 |
| 4 | Digitoxin | 670.0 ± 105.0 | 1.37 | 3.34 | 0.31 ± 0.03 |
| 5 | Dihydro-digitoxin | 800.0 ± 112.0 | 1.42 | 3.40 | 32.40 ± 2.85 |
| 6 | β-Methyldigitoxin | 1300.0 ± 227.0 | 1.71 | 8.28 | 0.40 ± 0.03 |
| 7 | Digoxigenin | 13.5 ± 2.3 | −0.02 | 0.36 | 10.70 ± 0.78 |
| 8 | Digitoxigenin-mono-digitoxoside | 12.7 ± 0.6 | 0.01 | 0.37 | 1.13 ± 0.08 |
| 9 | Digitoxigenin-bis-digitoxoside | 17.4 ± 2.0 | 0.15 | 0.44 | 1.06 ± 0.08 |
| 10 | Digoxin | 18.4 ± 2.0 | 0.25 | 0.50 | 0.90 ± 0.07 |
| 11 | Dihydro-digoxin | 25.0 ± 4.7 | 0.24 | 0.51 | 40.90 ± 3.35 |
| 12 | α-Methyldigoxin | 56.6 ± 9.8 | 0.54 | 1.13 | 2.23 ± 0.11 |
| 13 | β-Methyldigoxin | 63.3 ± 20.9 | 0.59 | 1.19 | 1.55 ± 0.06 |
| 14 | α,β-Dimethyldigoxin | 138.0 ± 12.1 | 0.94 | 2.76 | 1.28 ± 0.06 |
| 15 | α-Acetyldigoxin | 54.6 ± 7.8 | 0.50 | 0.99 | 2.50 ± 0.31 |
| 16 | β-Acetyldigoxin | 99.2 ± 4.1 | 0.70 | 1.25 | 1.60 ± 0.02 |
| 17 | α,β-Diacetyldigoxin | 392.0 ± 82.0 | 1.16 | 4.31 | 1.27 ± 0.02 |
| 18 | 12-Acetyldigoxin | 195.0 ± 17.5 | 0.89 | 1.60 | 20.90 ± 0.98 |
| 19 | 12-Acetyl-β-methyldigoxin | 746.0 ± 71.3 | 1.26 | 4.04 | 25.55 ± 1.70 |
| 20 | Gitoxigenin | 44.1 ± 1.8 | 0.38 | 0.67 | 21.37 ± 0.97 |
| 21 | Gitoxigenin-mono-digitoxoside | 60.1 ± 10.0 | 0.46 | 0.83 | 2.56 ± 0.21 |
| 22 | Gitoxin | 48.0 ± 11.2 | 0.68 | 1.28 | 2.55 ± 0.14 |
| 23 | 16-Formylgitoxin | 110.9 ± 6.2 | 0.84 | 1.82 | 0.78 ± 0.01 |
| 24 | Pentaformylgitoxin | 1440.0 ± 118.3 | 1.85 | 8.99 | 0.23 ± 0.00 |
| 25 | 16-Acetylgitoxin | 144.0 ± 32.8 | 0.89 | 2.27 | 0.85 ± 0.01 |
| 26 | Pentaacetylgitoxin | 2890.0 ± 668.0 | 1.86 | 49.45 | 112.00 ± 10.70 |
| 27 | k-Strophanthidin | 3.60 ± 0.5 | −0.14 | 0.42 | 17.80 ± 0.81 |
| 28 | k-Strophanthin-α | 4.40 ± 0.3 | −0.09 | 0.79 | 1.29 ± 0.14 |
| 29 | k-Strophanthin-β | 0.11 ± 0.01 | −0.50 | 0.22 | 2.51 ± 0.12 |
| 30 | k-Strophanthin-γ | 0.15 ± 0.07 | −0.62 | 0.21 | 2.47 ± 0.25 |

TABLE 1-continued

Partition co-efficients in Octanol/water system.
LIPOPHILICITY OF CARDIAC GLYCOSIDES
Table 1 The partition coefficients (P) in octanol/water system, $R_{ot}$ values
for the reversed-phase thin layer chromatography (mobile phase: methanol/water 30:70),
retentions (K') for the reversed-phase high pressure liquid
chromatography (eluent acetonitrile/water 45:55) and the $ID_{50}$ values
of inhibitory effects of the cardiotonic steroids on the guinea-pig heart
$Na^+$-$K^+$-ATPase

| Cardenolides | P | $R_{ot}$ | K' | $ID_{50}$ ($\times 10^{-4}$ mol $l^{-1}$) |
|---|---|---|---|---|
| 31 Ouabain (g-strophanthin) | 0.02 ± 0.00 | −0.73 | 0.14 | 2.28 ± 0.10 |
| 32 Dihydro-ouabain | 0.20 ± 0.00 | −0.71 | 0.15 | 45.50 ± 3.90 |

The standard deviations for the $R_{ot}$- and $K^+$-values were negligible (<4%) and have therefore been omitted.

In Table 2, the data in the column labeled "IC-50, nmol/L, cells" are concentrations of different cardiac glycosides that suppress spontaneous IL-8 secretion by 50%. The data are calculated from three independent experiments, with each individual experiment based on triplicate analysis. Experimental details are exactly as described in Srivastava et al., 2004. From the above results, it is evident that oleandrin and digitoxin are the most potent at suppressing IL-8 expression from cystic fibrosis lung epithelial cells. Furthermore, the data also indicate that specific structural modifications can significantly reduce potency.

The Structure-Activity Relationship (SAR) for cardiac glycosides can be elucidated from consideration of the relative activities of structural analogues. As seen from the structures shown in FIGS. 5A through 5H, the most active species tested (i.e., Species I, oleandrin, FIG. 5A; and Species II, digitoxin, FIG. 5B) are characterized by sugars of different structures and by the absence of oxygen-containing substitutions at or near the 12 position on the C ring. The next most active species (i.e., Species III, digoxin, FIG. 5C, and Species IV, ouabain, FIG. 5D) are also characterized by sugars of different structures. However, digoxin (Species III) has an equatorial hydroxyl moiety on the 12 position of the C ring, while ouabain (Species IV) has an axial hydroxyl on the neighboring 11 position of the C ring. Information on the contribution of sugars at the C3-OH position and oxygen at the C11 or C12 positions are summarized in Table 3, which illustrates the structure-activity-relationship (SAR) for cardiac glycosides, relative to digitoxin.

TABLE 2

Human dose calculation based on 50% reduction in IL-8 secretion from cystic fibrosis lung epithelial cells, and human toxicity limits from the literature.

| DRUG | IC50, nM based on human cell assay, nM (nmol/L) | Human dose, for 70 kg human calculated from IC50, mg [1] | Human dose for 70 kg human, nmoles | Human toxicity limit for 70 kg human, mg | Human toxicity limit for 70 kg human nmoles | Human toxicity limit, measured in serum or plasma, nM (nmol/L) |
|---|---|---|---|---|---|---|
| 1. oleandrin | 2.0 | 0.11 | 138 | UNK | UNK | UNK |
| 2. digitoxin | 0.9 | 0.05 | 66 | >2.5 | 3036 | >45.4 |
| 3. digoxin | 27 | 1.5 | 1900 | ≥1.5 [4] | 1900 | >27.1 |
| 4. ouabain | 8 | 0.30 | 510 | ≥1.0; lethal [2,3] | 1683 | >24.0 |
| 5. digoxigenin | 34 | 0.97 | 2500 | UNK | UNK | UNK |
| 6. digitoxigenin | 74 | 2.10 | 5500 | UNK | UNK | UNK |
| 7. acetylstrophanthdin | 117 | 3.40 | 8400 | UNK | UNK | UNK |
| 8. digoxigenin 3,12 diAC | >1000 | >27 | >50,000 | UNK | UNK | UNK |

[1] Human dose in milligrams ("mg"), for a standard 70 kg human, corresponding to the CF cell data, given in nmol/L ("nM"), for 50% reduction in anti-inflammatory activity.
[2] "Estimated Lethal Dose" of ouabain for human, based on Micromedex Health Care Series (http://www.thomsonhc.com). HAZARD-STEXT ® Hazard Response Management.
[3] The lethally toxic dose of ouabain in humans is ca. 1 mg/70 kg man (see note #2), corresponding to a concentration 24 nM (=24 nanomoles/L) (see note #2).
[4] The toxic dose of digoxin in humans is ca. 1.5 mg/70 kg man, corresponding to a concentration of 27 nM (=27 nanomoles/L), based on Micromedex Healthcare Series (http://www.thomsonhc.com). Digoxin, Section 3.3.2.

TABLE 3

Structure-Activity Relationships for Cardiac Glycosides

| Drug | # Sugars at C3-OH | Oxygen at C11 or C12 | Potency relative to digitoxin, % |
|---|---|---|---|
| Digitoxin | 3 | No | 100 |
| Oleandrin | 1 | No | 43 |
| Ouabain | 1 | Yes, C11 | 11 |
| Digoxin | 3 | Yes, C12 | 3.3 |
| Digeoxigenin | 0 | Yes, C12 | 2.6 |
| Digitoxigenin | 0 | No | 1.2 |
| Acetyl-stropanthidin | 0 | NO | 0.8 |

TABLE 3-continued

Structure-Activity Relationships for Cardiac Glycosides

| Drug | # Sugars at C3-OH | Oxygen at C11 or C12 | Potency relative to digitoxin, % |
|---|---|---|---|
| Digitoxigenin 3,12 di-Acetyl | 0 | Yes, C12 | <<0.1, inactive |

Potency declines with progress down the Table 2 entries. Species V also has an equatorial hydroxyl moiety on the 12 position, and also lacks sugars on the 3-OH position. Species VI lacks oxygen-containing substitutions on or near C-12; however, it also lacks sugars on the 3-OH. The next most active species (i.e., Species VII) also lacks both sugars on the 3 position and substitutions on the C ring. However, it has an equatorial carbonyl on the 19 position between the A and B rings. In all other compounds except Species IV, this position is occupied by an equatorial methyl group. Finally, we come to Species VIII which appears to be entirely inactive even at a concentration of 1000 nM (1 micromolar). Species VIII is characterized by an equatorial acetyl group at the 12 position of the C ring, as well as an acetyl group on the 3 position. This position is usually occupied in other species by sugar moieties.

From the above data, it appears that the activity of oleandrin and its analogues is optimally promoted by (i) the presence of glycosyl moieties at the 3 position of the sterol nucleus and (ii) by the absence of oxygen-containing substitutions at or near the 12 position on the C ring. Activity appears to decline when (i) glycosyl moieties are absent from the 3 position and when (ii) oxygen-containing substitutions are made at or near the 12 position on the C ring.

Additionally, activity is apparently altogether lost (e.g., Species VIII) when a bulky equatorial, oxygen-rich acetyl group is substituted at the 12 position. The equatorial 12 position and its neighbors therefore have negative pharmacophoric importance, whereas glycosidic substitution at the 3 position has a positive pharmacophoric importance for the control of IL-8 secretion from cystic fibrosis lung epithelial cells.

In the class of cardiac glycoside compounds, there are other species which possess the negative pharmacophoric importance of oxygen-containing substitutions on or near the C12 position. These include, but are not limited to, bufalin, proscillaridin and peruvoside.

In addition to the structure-activity-relationships defined above for optimal anti-inflammatory activity of cardiac glycosides, the lipophilic character, as defined by the octanol/water (20 mM TRIS-HCl, pH 7.4) partition coefficient ("P") can also be included as seen in Table 1. Higher P values indicate a greater proportion of the solute in the octanol, and therefore more lipophilicity by the cardiac glycoside. In a series of cardiac glycosides (Dzimiri et al, 1987), the order of decreasing P value is as follows: digitoxin (P=670)>digoxin (P=18.4)>>Ouabain (P=0.02). For applications to the central nervous system, where penetration through the Blood Brain Barrier is important, a high value for the permeability co-efficient, P, permits access in proportion to the value of P.

Inflammation and/or IL-8 lowering compositions of the invention typically comprise an anti-inflammatory or IL-8 lowering compound which may be formulated with one or more pharmaceutically acceptable carriers, excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. IL-8 and/or inflammation lowering amounts will be readily determined by those of ordinary skill in the art, depending on clinical and patient-specific factors.

In some embodiments, suitable effective dosages are those presented in Table 2, which illustrates the human dose calculation for specific cardiac glycosides, based on the 50% reduction data on IL-8 secretion from cystic fibrosis lung epithelial cells, and the relationship of these values to human toxicity limits obtained from the authoritative literature. This table shows therapeutic amounts of digitoxin, and some other cardiac glycosides that could be given to humans for reduction of IL-8 expression, as well as human toxicity limits, where known. The left hand panel in Table 2 reiterates the IC50 (50% inhibitory concentration) shown in Table 2 for suppression of IL-8 secretion by human CF lung epithelial cells. The middle panel in Table 2 calculates the dose of digitoxin and other cardiac glycosides which could be given to a 70 kg human, which would match the IC50 concentration measured by experiments with human CF lung cells. For convenience, the values are given in milligrams (mg), nanomols (nmol), and nanomolar (nmol/L, or nM). The right hand panel in Table 2 shows the toxicity-limited upper values of possible administration in milligrams (mg), nanomoles (nmol) and nanomolar (nanomoles/L, or nM).

The data in Table 2 indicate that the most potent of these cardiac glycosides is digitoxin. In the case of digitoxin, the inhibitory concentration, i.e. IC-50 dose for suppressing inflammation corresponds to 0.05 mg for a typical 70 Kg human, while the toxicity-limited upper level of administration is 2.3-3.4 mg. (Micromedix Healthcare Series (http://www.thomsonhc.com), Digitoxin, Section 2.2.2). Thus for digitoxin, the amount that could be theoretically given to suppress IL-8 expression by 50% is substantially far away from the toxicity limit. By comparison, for digoxin, the IC50 value (1.5 mg/70 kg human) is the same range as the toxicity-limited upper level of administration (0.9 to 1.5 mg, (Micromedix Healthcare Series (http://www.thomsonhc.com), Digoxin, Section 3.3.2)). Similarly, in the case of ouabain, the calculated IC50 dose is 0.3 mg for a typical 70 Kg man. However, the therapeutic range is limited by the fact that a mere 3-fold elevation in concentration to 1.0 mg is authoritatively considered lethal to humans. The "Estimated Lethal Dose" of ouabain for humans is based on the Micromedex Health Care Series, HAZARDSTEXT® (http://www.thomsonhc.com) Hazard Response Management. Thus the non-lethal toxicity-limited upper level of administration for ouabain is in the vicinity of the calculated IC50. Therefore, neither ouabain nor digoxin is suitable candidates as drugs for suppression of IL-8 production in vivo.

The lethal toxicity of cardiac glycosides for normal human cells is more than an order of magnitude greater than the toxicity levels measured for intact humans. For example, ouabain is lethally toxic to cultured human vascular endothelial cells (HUVEC), in vitro, with a 50% kill concentration of a 50% kill concentration of ca. 240 nM (240 nanomol/L, or [$2.4 \times 10^{-7}$ M]; Qie et al, 2008a); or, according to Ark et al (2010), ca. 357 nM (360 nanomols/L, or [$3.57 \times 10^{-7}$ M). In the case of digoxin, the 50% kill concentration for HUVECs is ca. 210 nM (210 nanomols/L, or [$2.10 \times 10^{-7}$ M]; Qiu et al, 2008b).

The amount, timing and mode of delivery of compositions of the invention comprising an anti-inflammatory and/or IL-8 lowering effective amount of a cardiac glycoside will be routinely adjusted on an individual basis, depending on such factors as weight, age, gender, and condition of the individual, the acuteness of the IL-8 hyper expression and/or related symptoms, whether the administration is prophylactic or therapeutic, and on the basis of other factors known to effect drug delivery, absorption, pharmacokinetics, including half-life, and efficacy.

An effective dose or multi-dose treatment regimen for the instant anti-inflammatory and/or IL-8 lowering formulations will ordinarily be selected to approximate a minimal dosing regimen that is necessary and sufficient to substantially prevent or alleviate inflammation and/or IL-8 hyper expression in the subject, and/or to substantially prevent or alleviate one or more symptoms associated with inflammation and/or IL-8 hyper expression in the subject. A dosage and administration protocol will often include repeated dosing therapy over a course of several days or even one or more weeks or years. An effective treatment regime may also involve prophylactic dosage administered on a day or multi-dose per day basis lasting over the course of days, weeks, months or even years. The activity can be enhanced in its affinity for this receptor by adding a hydrophobic group to region of the drug, thereby enhancing its interaction with the receptor at the expense of reducing interactions with the aqueous solvent. In the case of cardiac glycosides, converting an —OH group on the terminal sugar of the glycosyl moeity to an —$OCH_3$ has had the consequence of increasing the octanol/water coefficient. In the case of digitoxin (p=680) the B-methyl digitoxin which has such a group on the end has a much different value (P=1300). This modification can also be used on a small RNA, such as but not limited to siRNA or microRNA, to enhance its stability in the digestive tract if the microRNA is given to a mammal by mouth. The microRNA will not be digested in the stomach (it is not dissolved in water or aqueous solutions as easily), and thus passes through the digestive system to be utilized by the body without changing or being destroyed. Thus, the small RNA or micro RNA which is given can be utilized like a drug, or can be a drug in and of itself or can be an adjunct to a drug.

Various assays and model systems can be readily employed to determine the therapeutic effectiveness of the anti-inflammatory and/or IL-8 lowering treatment according to the invention. For example, blood tests such as an ELISA may be performed to measure the amount of IL-8. Clinical evaluations may be used to measure a decrease in the symptoms of diseases and conditions associated with IL-8.

The secondary or adjunctive therapeutic agents used in combination with, e.g., a cardiac glycoside in these embodiments may possess direct or indirect anti-inflammatory and/or IL-8 lowering activity alone or in combination with, e.g., a cardiac glycoside, or may exhibit other useful adjunctive therapeutic activity in combination with, e.g., a cardiac glycoside. A small siRNA or microRNA, such as the microRNAs that digitoxin affects to suppress reading out the EMT genes and/or reduce inflammation, can be used as an adjunct therapy to enhance the effects of digitoxin. Other useful adjunctive therapeutic agents in these combinatorial formulations and coordinate treatment methods include, for example, aspirin (acetyl ester), deflourophenyl, acetominiphen, indomethacin (methylated indole), sulindac, etoldoloc, mefenamic acid, meclofenamate, flufenamic acid, tolmetin, ketorolac, diclofenac, ibuprofen, naproxen, fenoprofen, ketoprofen, flurbiprofen, oxaprozin, piroxicam, meloxicam, mabumetone, celecoxib, valdecoxib, infliximab, adalimumab, etanercept; antidepressants such as selective serotonin reuptake inhibitors including, but not limited to, citalopram, escitalopram oxalate, paroxetine, fluoxetine, fluvoxamine maleate, and sertraline; monoamine oxidase inhibitors including, but not limited to, isocarboxazid, moclobemide, phenelzine, tranylcypromine, and selegiline; tricyclics including, but not limited to, amitriptyline, clomipramine, desipramine, dosulepin, doxepin, imipramine, nortriptyline, protriptyline, trimipramine, and lofepramine; tetracyclics, including, but not limited to, maprotiline, amoxapine, mianserin, and mirtazapine; anxiolytics drugs including, but not limited to, bupropion, duloxetine, nefazodone, and reboxetine; norepinephrine reuptake inhibitors; trazodone; venlafaxine; tianeptine; milnacipran; antisychotics including, but not limited to, butyrophenones such as haloperidol and droperidol; phenothiazines such as chlorpromazine, fluphenazine, perphenazine, prochlorperazine, thioridazine, trifluoperazine, mesoridazine, promazine, triflupromazine, levomepromazine/methotrimeprazine, promethazine, and pimozide; thioxanthenes including, but not limited to, chlorprothixene, flupenthixol, thiothixene, and zuclopenthixol; second generation antipsychotics including, but not limited to, clozapine, olanzapine, risperidone, quetiapine, ziprasidone, amisulpride, asenapine and paliperidone; third generation antipsychotics including, but not limited to, aripiprazole, bifeprunox, norclozapine (ACP-104), tetrabenazine and cannabidiol. Additional secondary or adjunctive therapeutic agents may include TNF-alpha superfamily ligands including, but not limited to, APRIL (A proliferation-inducing ligand), FAS ligand (FASL), CD30 ligand (CD3OL), CD4OL, 4-1BBL, gp34, TRAIL (TNFalpha Inducing Ligand), RANKL (Receptor activator of NFkB RANK ligand), BAFF, CD27 ligand, EDA, EDA-A1, EDA-A2, GITR ligand, LIGHT, TL1A, and TWEAK, as well as vitamin therapy such as ascorbic acid.

Digitoxin and related cardiac glycosides can also be utilized as adjuvant therapies to accompany the use of anti-cancer drugs, or combinations of anti-cancer drugs. These drugs include, but are not limited to, (i) alkylating agents, including cisplatin, carboplatin, oxaliplatin, mechlorethamine, cyclophosphamide, chlorambucil and ifosfamide; (ii) antimetabolites, including azathioprine, mercaptopurine; (iii) plant alkaloids and terpinoids, including vinca alkaloids such as vincristine, vinblastin, vinorelbine, and vindesine; and taxanes, such as taxol and docetaxel; (iv) topoisomerase inhibitors, such as the camptothecins irinotecan and topotecan; and type II inhibitors such as amsacrine, and podophyllotoxins, such as the etoposide, etoposide phosphate and teniposide; (v) cytotoxic antibiotics, such as actinomycin; anthracycclines such as doxorubicin, daunamycin, valrubicin, idarubicin; miscellaneous small molecules, including bleomycin, plicamycin and mitomycin; (vi) nanodrugs, including formulations of paclitaxel; (vii) electrotherapy; (viii) radiation therapy, including local radioactive agents such as radium and radio-iodine; and global radiation such as X-Ray, proton beam, carbon beam, and other ion beam therapies; (ix) differentiation therapies; (x) epithelial-mesenchymal transition (EMT) therapies.

Digitoxin may be useful in cancer treatment as a differentiation therapy agent. The concept of inducing the most aggressive metastatic cancers to become less aggressive, and more differentiated, has been termed differentiation therapy (Rane et al, 2012). The problem is that the metastatic cells eventually evolve away from sensitivity to the various chemo-therapeutic drugs, and resume robust growth. Adjuvant differentiation therapy is a strategy that gives the cancer stem cell the option of becoming more differentiated, and thus surviving in a state with slower growth potential (Rane et al, 2012). The re-differentiated cancer stem cells are then re-sensitized to the original chemotherapy agent. The mechanism may depend on actively proliferating progeny being preferentially eliminated, thereby allowing resistant cells to become selected from a relatively dormant tumor cell population (Kreso et al, 2013). This approach has actually been shown to work in only a few specific types of tumors, for example, anthrocycline-resistant acute promyelocytic leukemia (APL). Steroid glycosides, including digitoxin, have been reported to be able to induce mouse myeloid leukemia cells to a more differentiated phenotype in culture (Umehara et al, 1995). It is therefore possible that digitoxin might possess general adjuvant differentiation therapy activity.

Digitoxin may function as an inhibitor of Epithelial-Mesenchymal-Transition (EMT) by affecting gene transcription. Digitoxin may suppress genes from being read out that would have helped the metastisis to occur. Epithelial cancer cells that form at a primary site, and then metastasize to a second site, do so by initiating a program termed the epithelial mesenchymal transition (EMT). Once at the second site, the mesenchymal cells transition back into their epithelial character by a reverse process termed mesenchymla-epithelial transition (MET) (Hollier et al, 2009; Van Denderen and Thompson, 2013). Proinflammatory cytokines have been reported to promote the epithelial mesenchymal transition (EMT) in cancer cells (Jing et al, 2012). Consistently, increased IL-8 expression and increases in certain genes are closely correlated with epithelial mesenchymal transition (EMT) signaling in cancer (Yu et al, 2013). For example, significantly increased IL-8 protein expression is found in 90.91% of neurotensin-positive hepatocellular carcinomas (Yu et al, 2013). The latter investigators show that dysfunctional activation of the neurotensin/IL-8 pathway is associated with increased inflammatory response and enhanced EMT in cancer, and specifically a worse prognosis (Yu et al, 2013).

Consistently, Examples 4, 5 and 6 show that digitoxin (i) inhibits growth of the primary castration resistant prostate cancers; (ii) inhibits seeding and growth of metastases to the lung; (iii) inhibits expression of EMT genes (in rat PAIII castration resistant prostate cancer cells) and proteins (in human PC3 castration resistant prostate cancer cells); and (iv) inhibits expression of IL-6 and CINC1 (the rat equivalent of IL-8) in sera of digitoxin-treated rats bearing PAIII cancers. Therefore, cardiac glycosides such as digitoxin, that inhibit IL8 expression in cancer cells and/or inhibit the transcription of certain genes, may prove useful for inhibiting the EMT/MET transition processes.

As noted above, in all the various embodiments of the invention contemplated herein, the anti-inflammatory and or IL-8 lowering methods and formulations may employ a cardiac glycoside compound in any of a variety of forms, including any one or combination of the subject compound's pharmaceutically acceptable salts, isomers, enantiomers, polymorphs, solvates, hydrates, and/or prodrugs. In exemplary embodiments of the invention, oleandrin is employed within the therapeutic formulations and methods for illustrative purposes.

The pharmaceutical compositions of the present invention may be administered by any means that achieve their intended therapeutic or prophylactic purpose. Suitable routes of administration for the compositions of the invention include, but are not limited to, oral buccal, nasal, brachytherapy, aerosol, topical, transdermal, mucosal, injectable, slow release, controlled release, iontophoresis, sonophoresis, and including all other conventional delivery routes, devices and methods. Injectable methods include, but are not limited to, intravenous, intramuscular, intraperitoneal, intraspinal, intrathecal, intra cerebroventrivular, intraarterial, subcutaneous and intranasal routes.

The compositions of the present invention may further include a pharmaceutically acceptable carrier appropriate for the particular mode of administration being employed. Dosage forms of the compositions of the present invention include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives.

If desired, the compositions of the invention can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps or other biocompatible matrices such as cholesterol.

Compositions of the invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose, dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets, which may be prepared by any conventional method of preparing pharmaceutical oral unit dosage forms. Oral unit dosage forms, such as tablets, may contain one or more conventional additional formulation ingredients, including, but not limited to, release modifying agents, glidants, compression aides, disintegrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum, and glyceryl monostearate. Substances which may be used for coating include hydroxypropyl cellulose, titanium oxide, talc, sweeteners and colorants.

Additional compositions of the invention can be prepared and administered in any of a variety of inhalation or nasal delivery forms known in the art. Devices capable of depositing aerosolized purified cardiac glycoside formulations in the sinus cavity or pulmonary alveoli of a patient include metered dose inhalers, nebulizers, dry powder generators, sprayers, and the like. Methods and compositions suitable for pulmonary delivery of drugs for systemic effect are well known in the art. Additional possible methods of delivery include deep lung delivery by inhalation. Suitable formulations, wherein the carrier is a liquid, for administration, as for example, a nasal spray or as nasal drops, may include aqueous or oily solutions of cardiac glycosides and any additional active or inactive ingredient(s).

Further compositions and methods of the invention are provided for topical administration of cardiac glycoside for reducing the inflammation and/or IL-8 production in cells that are overproducing IL-8. Topical compositions may comprise a cardiac glycoside along with one or more additional active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise a cardiac glycoside dissolved or dispersed in a portion of water or other solvent or liquid to be incorporated in the topical composition or delivery device. It can be readily appreciated that the transdermal route of administration may be enhanced by the use of a dermal penetration enhancer known to those skilled in the art. Formulations suitable for such dosage forms incorporate excipients commonly utilized therein, particularly means, e.g. structure or matrix, for sustaining the absorption of the drug over an extended period of time, for example, 24 hours. Transdermal delivery may also be enhanced through techniques such as sonophoresis. Yet additional cardiac glycosides of the invention are designed for parenteral administration, e.g. to be administered intravenously, intramuscularly, subcutaneously or intraperitoneally, including aqueous and non-aqueous sterile injectable solutions which, like many other contemplated compositions of the invention, may optionally contain anti-oxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers. Additional compositions and formulations of the invention may include polymers for extended release following parenteral administration. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts. Parenteral preparations typically contain buffering agents and preservatives, and injectable fluids that are pharmaceutically and physiologically acceptable such as water, physiological saline, balanced salt solutions, aqueous dextrose, glycerol or the like. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In more detailed embodiments, compositions of the invention may comprise a cardiac glycoside encapsulated for delivery in microcapsules, or attached to nanoparticles, microparticles, or microspheres, prepared, for example, by coacervation techniques or by interfacial polymerization, for example, hydroxymethylcellulose or gelatin-microcapsules and poly(methylmethacylate) microcapsules, respectively; in colloidal drug delivery systems (for example, liposomes, albumin microspheres, microemulsions, nano-particles and nanocapsules); or within macroemulsions.

As noted above, in certain embodiments the methods and compositions of the invention may employ pharmaceutically acceptable salts, e.g., acid addition or base addition salts of the above-described cardiac glycoside. Examples of pharmaceutically acceptable addition salts include inorganic and organic acid addition salts. Suitable acid addition salts are formed from acids which form non-toxic salts, for example, hydrochloride, hydrobromide, hydroiodide, sulphate, hydrogen sulphate, nitrate, phosphate, and hydrogen phosphate salts. Additional pharmaceutically acceptable salts include, but are not limited to, metal salts such as sodium salts, potassium salts, cesium salts and the like; alkaline earth metals such as calcium salts, magnesium salts and the like; organic amine salts such as triethylamine salts, pyridine salts, picoline salts, ethanolamine salts, triethanolamine salts, dicyclohexylamine salts, N,N'-dibenzylethylene-diamine salts and the like; organic acid salts such as acetate, citrate, lactate, succinate, tartrate, maleate, fumarate, mandelate, acetate, dichloroacetate, trifluoroacetate, oxalate, and formate salts; sulfonates such as methanesulfonate, benzenesulfonate, and p-toluenesulfonate salts; and amino acid salts such as arginate, asparginate, glutamate, tartrate, and gluconate salts. Suitable base salts are formed from bases that form non-toxic salts, for example aluminum, calcium, lithium, magnesium, potassium, sodium, zinc and diethanolamine salts.

In other detailed embodiments, the methods and compositions of the invention employ prodrugs of cardiac glycosides. Prodrugs are considered to be any covalently bonded carriers which release the active parent drug in vivo. Examples of pro-drugs useful within the invention include esters or amides with hydroxyalkyl or aminoalkyl as a substituent, and these may be prepared by reacting such compounds as described above with anhydrides such as succinic anhydride.

The invention disclosed herein will be understood to encompass methods and compositions comprising cardiac glycosides or their byproducts. These byproducts include, but are not limited to genes, such as small RNAs (siRNAs) or microRNAs. These metabolic products of the cardiac glycosides can be directly administered in the form of the siRNA or the microRNA itself. If the mammal has too little of the small RNA, the mammal may need it to be raised either by giving more of the cardiac glycoside or by giving the mammal a supplement of the small RNA or microRNA directly or a mimic. If the mammal has too much, it may need to have an "antagomir", an anti-miRNA to lower it. If given orally, these products may need to be changed to "mimics", which are versions modified with the ending ribose changed to a 2-O—$CH_3$. Changing the small RNA in this manner protects it from being digested when given orally as a therapeutic.

In other embodiments these products may result for example from the oxidation, reduction, hydrolysis, amidation, esterification, glycosylation and the like of the administered compound, primarily due to enzymatic processes. Accordingly, the invention includes methods and compositions of the invention employing compounds produced by a process comprising contacting a cardiac glycoside with a mammalian subject for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein will also be understood to encompass diagnostic compositions for diagnosing the risk level, presence, severity, or treatment indications of, or otherwise managing a condition in a mammalian subject caused by or exacerbated by inflammation and/or excessive IL-8 production, comprising contacting a labeled (e.g., isotopically labeled, fluorescent labeled or otherwise labeled to permit detection of the labeled compound using conventional methods) cardiac glycoside to a mammalian subject (e.g., to a cell, tissue, organ, or individual) at risk or presenting with one or more symptom(s).

The invention disclosed herein will also be understood to encompass diagnostic compositions for diagnosing the risk level, presence, severity, or treatment indicative of, or otherwise managing, a metabolic disorder disease, or condition, in a mammalian subject, comprising contacting a labeled (e.g., isotopically labeled, fluorescent labeled or otherwise labeled to permit detection of the labeled compound using conventional methods) cardiac glycoside to a mammalian subject (e.g., to a cell, tissue, organ, or individual) at risk or presenting with one or more symptom(s) of metabolic disorders, and thereafter detecting the presence, location, metabolism, and/or binding state of the labeled compound using any of a broad array of known assays and labeling/detection methods.

In exemplary embodiments, a cardiac glycoside is isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as 2H, 3H, 13C, 14C, 15N, 18O, 31P, 35S, 18F and 36C, respectively. The isotopically-labeled compound is then administered to an individual or other subject and subsequently detected as described above, yielding useful diagnostic and/or therapeutic management data, according to conventional techniques.

While the instant invention has been shown and described herein in what are conceived to be the most practical and preferred embodiments, it is recognized that departures may be made therefrom within the invention, which is therefore not to be limited to the details disclosed herein, but is to be afforded the full scope of the claims so as to embrace any and all equivalent apparatus and articles. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list.

All publications and patents cited herein are incorporated herein by reference for the purpose of describing and disclosing, for example, the materials and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

From the foregoing, it will be appreciated that, although specific embodiments of the invention have been described herein for purposes of illustration, various modifications may be made without deviating from the spirit and scope of the appended claims.

Examples include (1) lung disorders, including but not limited to, cystic fibrosis, asthma, bronchial hyper-responsiveness syndrome, chronic obstructive pulmonary disease (COPD), interstitial pneumonia, interstitial pneumonia, necrotizing nosocomial pneumonia ("NP"), influenza, acid injury to the lung, re-expansion pulmonary edema (REPE), endotoxemia-induced respiratory distress syndrome, and smoke inhalation; (2) diabetic conditions, including but not limited to, type I diabetes, type II diabetes, and diabetic retinopathy; (3) immune system disorders such as arthritis syndromes, including but not limited to, rheumatoid arthritis, psoriasis, psoriatic arthritis, Sjogren's disease, ankylosing spondylitis, and Behcet's disease, inflammatory bowel disease, Familial Mediterranean Fever, Lupus, Chronic Granulomatous Disease (CGD); (4) brain disorders, including but not limited to, epilepsy, stroke, traumatic brain injury, Alzheimer's disease, Parkinson's disease, Huntington's disease and other poly-glutamine diseases such as spinocerebeller muscular atrophy, dento-rubropallido luysian atrophy, and other forms of spino-cerebellar atrophy, brain cancer, cerebral hyperfusion injury, traumatic brain injury, stroke; (5) viral diseases, including but not limited to, HIV, HIV-associated dementia, AIDS, Influenza, rhinovirus (HRV), adenovirus, respiratory syncytial virus (RSV), and herpes virus, increases in cytokines following viral infections; (6) transplant graft rejection, including but not limited to, kidney transplant graft rejection, bladder transplant graft rejection, pancreas transplant graft rejection, heart transplant graft rejection, lung transplant graft rejection, liver transplant graft rejection, and multiple organ transplant graft rejection; (7) heart disease, including but not limited to, heart failure, cardiac arrest, atherosclerosis, and cardiopulmonary bypass surgery; (8) gastrointestinal diseases, including but not limited to, inflammatory bowel disease, ulcerative colitis, Crohn's disease, and acute pancreatitis; (9) syndromes following resolved bacterial infection, including but not limited to, glomerulonephritis, and Kowasaki syndrome; (10) cancer, including but not limited to, prostate cancer including hormone resistant prostate cancer, endocrine cancers such as pancreatic cancer, lung cancer, skin cancers including head and neck squamous cell carcinoma, malignant melanoma, colorectal cancer, bladder cancer, ovarian cancer, breast cancer, glioblastoma, and osteogenic sarcoma; (11) skin disorders including but not limited to, burns, psoriasis, cancer; and (12) miscellaneous conditions, including but not limited to, fevers resistant to cyclooxygenase inhibitors, sepsis, endometriosis, parasitic infections including schistosomiasis, systemic lupus erythematosus, and thermal injuries, including sun burn. These are elaborated in the following section.

1. Lung Disorders

Cystic Fibrosis (CF), the most common, life limiting autosomal recessive genetic disease in the U.S., principally characterized by hyper expression of IL-8 in the airway. The major source of IL-8 in the CF airway is the airway epithelium, and the resulting high levels of IL-8 attract a massive and sustained influx of neutrophils and other inflammatory cells. The CF epithelial cells also secrete high levels of other proinflammatory cytokines, but they are far less potent than IL-8. The molecular basis for IL-8 hypersecretion in the CF lung is known to be a dysfunctional TNFa/NFKB signaling pathway. For that reason an attractive pharmaceutical strategy has been to find a drug that would suppress that part of the pathway involved in IL-8 expression, but not other parts required for physiological responses to infection.

Consistently, airway epithelial cells isolated from cystic fibrosis patients secrete more IL-8 than do cells cultured from patients without cystic fibrosis (Bedard, et al. (1993); Ruef, et al. (1993); Dimango, et al. (1998)). Interestingly, cells cultured from much higher in the airway, such as those from the nasal epithelium, do not show this disparity between control and cystic fibrosis patients (Black et al. (1998)). In addition, cystic fibrosis respiratory epithelial cells are hyper-responsive in terms of IL-8 secretion to *Pseudomonas* cells and toxins (Massion et al. (1994); Dimango, et al. (1998)), or to a combination of TNFa and INFy (Schweibert, et al. (1999)). The disease is caused by recessive mutations in the Cystic fibrosis transmembrane conductance regulator (CFTR) gene, and levels of the CFTR protein in human lung are highest in submucosal glands. High levels of IL-8 mRNA and protein have been shown in this tissue from cystic fibrosis patients, in vitro. (Tabary, et al. (1998)). In the latter study, other pro-inflammatory cytokines such as IL-1 and IL-6 were unaffected by the cystic fibrosis condition. The high levels of IL-8 production by cystic fibrosis epithelial cells have been proposed to be due to retention of mutant CFTR in the endoplasmic reticulum, which, by an unknown mechanism, activates NFKB via activation of IkBalpha (DiMango et al. (1998)). Attention is drawn to the NFKB system because it is known that transcription of the IL-8 gene is activated in normal epithelial cells when activated NFKB migrates from the cytosol to the nucleus and binds to the IL-8 promoter. An adenovirus hyper expressing IkBalpha has been employed to suppress IL-8 secretion both from a cystic fibrosis cell line ("CFTE"), as well as from mouse lung (as MIP2), when instilled simultaneously with an infectious dose of *P. aeruginosa* (Griesenbach, et al. (1999); ibid (2000)). IL-8 secretion by the cystic fibrosis tracheal epithelial cell line IB-3 is elevated compared to IL-8 secretion by the same cell line corrected with wild type CFTR (Eidelman, et al. (2001 a)). Therefore, elevated levels of IL-8 secretion may be caused by mutant CFTR and a drug or gene able to correct the trafficking defect of AF508-CFTR may also lower IL-8 secretion.

Recently, low concentrations of the drug digitoxin have been discovered to suppress IL-8 hypersecretion by CF lung epithelial cells (Srivastava et al *PNAS,* 2004). The mechanism of digitoxin action is to suppress the TNFa/NFKB signaling pathway. Digitoxin specifically blocks the interaction between the TNF Receptor and the adaptor protein TRADD). This site of interaction is known as the initiator for assembly of a set of three other adaptor proteins, the TNFReceptor Signaling Complex, which leads downstream to IL-8 expression. (Yang et al, *PNAS* 2005).

Somewhat elevated IL-8 levels have been found in asymptomatic nonspecific airway hyperresponsiveness (BHR) (Betz, et al. (2001)). Patients with chronic obstructive pulmonary disease (COPD), sometimes used as a theoretical control for cystic fibrosis, also have high levels of IL-8 (Betz, et al. (2001)). The two problems are thought to be temporally related because it is thought that asymptomatic BHR can progress to COPD. From an acute point of view, multi-trauma patients often develop nosocomial pneumonia (NP), and a higher level of IL-8 in bronchoalveolar lavage fluids of the incoming patient is predictive of the development of NP (Muehlstedt, et al. (2001)). For these reasons, drugs that specifically target IL-8 production should be useful in treating or preventing asthma, BHR, COPD, and NP.

While IL-8 levels in cystic fibrosis lungs are tonically elevated over controls by factors of 1000 fold or more, much more modest levels of IL-8 elevation, in the range of 2 to 10 fold, have been noted in some other pulmonary diseases and disorders. Modest but significant elevations of IL-8 have been reported in noneosinophilic asthma (Gibson, et al. (2001)). IL-8 levels in asthmatic children are detectable, and are correlated with symptoms (Marguet, et al. (2001)).

Acid injury to the lung is associated with an increase in alveolar epithelial permeability to protein and a reduction in net alveolar fluid clearance (Modelska et al. (1999)). However, pretreatment with an anti-IL-8 antibody significantly reduces the acid mediated increase in bi-directional transport of protein across the alveolar epithelium, and restores alveolar fluid clearance to normal (Models et al. (1999)). Thus drugs capable of suppressing IL-8 should be useful therapeutics for acid injury to the lung.

Smoke inhalation, as found in victims of fires or injured firemen, causes lung endothelial injury and formation of pulmonary edema. Laffon, et al. (1999) have developed a rabbit model in which cooled smoke causes significant increases in alveolar epithelial permeability and a significant reduction in bidirectional transport of protein across the pulmonary epithelium. However, Laffon, et al. (1999) show that administration of an anti-IL-8 antibody restores alveolar epithelial permeability to normal levels and significantly increases bidirectional transport of protein. Thus increased IL-8 is an important mediator of lung injury following smoke inhalation, and drugs capable of suppressing IL-8 should be useful therapeutics for smoke inhalation problems affecting lung function.

Reexpansion pulmonary edema (REPE) often follows reexpansion of a collapsed lung due to a mechanism of increased microvascular permeability and inflammatory cell accumulation (Nakamura, et al. (2000)). Local overproduction of IL-8 is responsible for the process. Pretreatment with anti-IL-8 antibody significantly reduces the neutrophil count in bronchoalveolar lavage (BAL) fluid and suppresses REPE. Thus drugs capable of suppressing IL-8 should be useful therapeutics for reexpansion pulmonary edema in the lung.

2. Metabolic Disease Syndromes and Diabetes

Plasma IL-8 concentrations after glucose load are increased in obese subjects with impaired glucose tolerance in comparison to normoglycemic weight-matched individuals (Straczkowski et al., (2003)).

Additionally, diabetes, affecting 7% of the U.S. population, is associated with an approximately 4-fold elevation in ambient serum IL-8 (Zozulinska, et al. (1999)). The increment is valid for both Type I and Type II diabetics, and is significantly correlated with levels of glycosylated hemoglobin (HbA1C). The study was performed in a set of diabetic patients with no evidence of acute or chronic infection, renal failure or ketoacidosis, and a set of age-matched controls. Supportive data have been reported by Yuuki, et al. (2001). The IL-8 signal is a strong beacon for polymorphonuclear leukocytes, and the relationship is consistent with a pro-inflammatory phenotype for diabetes. It is thus likely that drugs that suppress baseline levels of IL-8 should be useful for the treatment of complications of diabetes.

One of the major complications in diabetes is vascular damage in the retina due to high glucose. Elner et al. (1995), report that significantly higher levels of IL-8 occur in the vitreous humor of diabetes patients with Proliferative Diabetic Retinopathy (PDR). In contrast, IL-8 levels in vitreous of non-diabetic patients with proliferative vitreoretinopathy, an analogous syndrome not associated with diabetes, are equivalent to control levels found in normal eyes. In addition, other conditions such as idiopathic macular holes, idiopathic macular puckers, vitreous hemorrhages, or uncomplicated retinal detachments have a phenotype of normal IL-8 levels in the vitreous. Yuuki, et al. (2001) also report that levels of IL-8 in vitreous fluids are greater in proliferative diabetic retinopathy (PDR) than in non-inflammatory retinopathy. Elner et al. (1998) report that elevated IL-8 levels can be found only in active cases of PDR, but not inactive PDR cases.

Temaru et al. (1997) show that high glucose concentrations induce elevated IL-8 mRNA expression in cultured human aortic endothelial cells, but not smooth muscle cells. These data are interpreted to suggest that diabetic macroangiopathy is caused by a glucose-dependent gradient of IL-8 between the smooth muscle and the arterial intima. Elner, et al. (1995 & 1998) interpret the data to suggest that IL-8 participates in the pathogenesis of proliferative diabetic retinopathy. For these reasons, drugs that specifically suppress IL-8 production should be useful in treating diabetic complications such as diabetic retinopathy.

3. Immune System Disorders

IL-8 and other chemokines have also been implicated in the pathogenesis of inflammatory bowel disease (Imada, et al. (2001)). The levels of IL-8 are especially elevated in acute organ cultures of patients with active ulcerative colitis. (Imada, et al., 2001) Ulcerative colitis is an inflammation of the colon, in which etiologically different types are known including autoimmune colitis such as inflammatory bowel disease and Crohn's disease, idiopathic colitis such as lymphocytic colitis and collagenous colitis, iatrogenic colitis caused by surgical or chemical intervention and vascular or ischemic colitis. High levels of IL-8 are expressed by colon cells and by inflammatory cells attracted to the focus of IL-8 production. Thus, inhibition of IL-8 production by cells in the inflamed colon may therefore be useful for treating ulcerative colitis, including Crohn's disease. The levels of IL-8 are especially elevated in acute organ cultures of patients with active ulcerative colitis. (Imada, et al., 2001).

Imada, et al. (2001) show that increased expression of IL-8 message can be detected in macrophages, pericrypt myofibroblasts, and epithelium. Dietary fat may exacerbate intestinal inflammation, and studies with monolayers of colon epithelial cells indicate that medium-chain fatty acids such as oleic acid cause a five-fold elevation of IL-8 secretion (Tanaka. et al. (2001)). The process follows the anatomy of digestion, since the fatty acid is added on the apical (lumenal) side, while IL-8 secretion occurs in the baso-lateral (serosal) direction. Thus drugs that interfere with IL-8 production should be useful in the treatment of inflammatory bowel disease.

Rheumatoid arthritis, afflicting approximately 1% of the population, is a chronic multisystem disease of unknown cause, characterized by persistent inflammatory synovitis, principally in symmetrical peripheral joints (Lipsky (2001)). High basal levels of IL-8 are found in synovial fluid and in synovial cells (Troughton, et al. (1996); Rothe, et al. (1998); Rodenburg et al. (1999); Olszewski, et al. (2001); Nanki, et al. (2001); Hayashida, et al. (2001)). It has been proposed that IL-8 participates in synovial lesions at the earliest stages of rheumatoid disease (Takahashi et al. (1999)) and that symptoms coincide with increased synthesis of IL-8 (Kraan et al. (2001)). The synthesis of IL-8 by synovial cells or tissues promotes ingress of peripheral monocytes (Hayashida, et al. (2001)), as well as angiogenesis, possibly to support the chronic inflammatory state (Koch, et al. (2001)). The mechanism of IL-8 synthesis by synovial cells involves the NFkB pathway (Morel, et al. (2001)) and increases in IL-8 mRNA. Certain other categories of arthritis are also characterized by high levels of IL-8, including Behcet's (Ertenli, et al. (2001)), psoriatic (Honig et al. (1997)), and Sjogren's (Amin, et al. (2001)). Therapy of rheumatoid arthritis by either methotrexate (Gao, et al. (1998)) or aurothioglucose (Yoshida. et al. (1999)) results in reduction of IL-8 levels in the affected joints. These data suggest that drugs able to interfere with IL-8 secretion in synovial tissues should be useful for treatment of rheumatoid and other types of IL-8 related arthritis.

Psoriasis is a disabling, proliferative skin disorder associated with systemic elevation of lymphocytes (Hoxtermann, et al. (1998)) and other evidences of aberrant cytokine production (Stoof, et al. (2001)). Stoof. et al. (2001)), in a study of the mechanism of action of the antipsoriatic drug dimethylfumarate (DMF), show that DMF, in the range of 5-50 pM, suppresses interferon-gamma-stimulated production of IL-8 and related cytokines by human karatinocytes. These cytokines are thought to be responsible for the perpetuation of psoriatic lesions.

Familial Mediterranean Fever (FMF) is an example of a class of disorders associated with the innate immune system in which there are seemingly unprovoked episodes of inflammation without high titer autoantibodies or antigen-specific T cells (Masters et al., 2009). FMF is caused by a recessive mutation in the MEFV gene, and causes high levels of circulating cytokines, including IL-8. (Notarnicola et al., 2002). High levels of IL-8 are found in the circulation of patients with an acute attack, but not during remission periods (Direskineli et al., 1999).

Chronic Granulomatous disease (CGD) is a general name for a group of immunodeficiency diseases associated with defective phagocytosis. CGD phagocytes such as neutrophils, monocytes and macrophages, have mutations in protein subunits associated with phagocyte NADPH oxidase (PHOX), which are required for killing ingested bacteria (Lekstrom-Himes and Gallin, 2000; Malech and Hickstein, 2007). IL-8 is overproduced by IL-10 stimulated CGD neutrophils (Lekstrom-Himes et al., 2005). Granulomas made up of CGD neutrophils, are formed by concerted attraction of CGD neutrophils for one another, possibly in response to spontaneously secreted cytokines and chemokines, including IL-8.

Systemic lupus erythematosus (SLE) is a systemic autoimmune disorder associated with high levels of IL-8 and other proinflammatory cytokines in the serum (Avramescu et al., 2010). In addition, IL-8 levels were higher in the cerebrospinal fluid from patients with neuropsychiatric SLE than with systemic SLE alone (Lu et al., 2010).

4. Brain Disorders

IL-8, ICAM-5, and other cytokine/chemokine production is closely related to temporal lobe epilepsy and related convulsive disorders in humans. For example, vagal nerve stimulation has been shown to suppress refractory epilepsy over many months of therapy, and, concommittantly to reduce IL-8 levels in the blood in the process (De Herdt et al, 2009). Additional information linking IL-8 and epilepsy has come from the finding that high levels of IL-8 are located in surgically obtained regions of brain associated with the origins of the seizures in children with intractable epilepsy (Choi et al, 2009). Induction of seizures by injection of kainic acid into the hypothalamus of rats has been shown to elevate IL-8 levels in the injected brain regions (Lauren et al, 2010). Youn et al (2012) have reported that neonatal seizures are associated with elevation of IL-8 in sera from these patients. In addition, drug resistant temporal lobe seizures in adult humans have recently been shown to be associated with significantly high levels of IL-8 in plasma (Pollard et al, 2013). Finally, it has been shown that digitoxin preferentially accumulates in the cerebrospinal fluid (Kuhlman et al, 1978; Storstein et al, 1979). Thus digitoxin has intrinsic access to the brain, where it might exercise its potential as an anti-convulsant agent.

Alzheimer's disease is the most common form of dementia. The apolipoprotein E4 allele has been implicated in atherosclerosis and Alzheimer's disease. Drabe et al. (2001) show that patients carrying the apolipoprotein E4 allele have higher baseline levels of IL-8 and TNFa than patients lacking this allele. It is believed to be due to toxic effects of brain-derived amyloid beta peptide (ABP). The pathological basis of ABP action on neurons is the increase in intracellular Ca2+ via calcium channels formed by the ABP itself (Arispe, et al. (1993); (1996)). Among the consequences of this action are increases in immune/inflammatory pathways associated with IL-8 in affected areas of the brain such as the cortex and hippocampus (Gitter, et al. (1995)).

During the inflammatory process, microglial release of proinflammatory cytokines act on the endothelium of blood-brain barrier (BBB) cells to stimulate upregulation of adhesion molecules. Consequently, this upregulation leads to the recruitment of passing T cells and monocytes, which express the counter receptors, that then go on to release more cytokines. Gitter, et al. (1995) show that Alzheimer's Disease related Amyloid Precursor Protein (APP) stimulates IL-8 secretion from human astrocytoma cells. In addition, IL-1beta potentiates Amyloid beta peptide (ABP) action on IL-8 secretion by astrocytes by 10-fold, a process which is altogether blocked by calcium chelators such as EGTA. The immediate target of the secreted IL-8 may be IL-8 receptors, which are plentiful in the central nervous system. Xia et al (1997) report that the IL-8 Receptor B protein colocalizes with ABP-positive neurites in Alzheimer's disease brain, but not with paired helical filaments (PHF) or hyperphosphorylated tau. Thus, while IL-8 may be important in normal brain for signaling between neurons and glia, the action in Alzheimer's disease brain may be to potentiate immune destruction of neurons. These data suggest that drugs that are able to interfere with IL-8 secretion in brain should be useful as therapeutics for Alzheimer's disease.

Parkinson's disease, caused by destruction of the substantia nigra pars compacta in the midbrain, joins Alzheimer's disease as one of the neurodegenerative disorders whose incidence is increasingly manifest in the aging population. Higher levels of proinflammatory cytokines are found in Parkinson's disease patients' brains, including IL-8 (Zhang et al, 2008), and inflammation is thought to be a major contributor to the neurodegeneration in the Parkinson's disease patients (Tansey et al, 2007). Polymorphisms of genes associated with the proinflammatory TNFa pathway have been discovered and interpreted as indicating an immunomodulatory effect on sporadic Parkinson's disease (Kruger et al. (2000); Nishimura, et al. (2001)). Nishimura et al. (2000) suggest that TNFa may have a toxic effect on Parkinson's disease, implying action at the level of the substantia nigra in the brain. MPTP (N-methyl-1-4 phenyl-1,2,3,6-tetrahydropyridine) is a neurotoxin which causes Parkinson's disease-like syndrome in organisms as phylogenetically diverse as goldfish and man (Pollard, et al. (1992); Goping, et al. (1995)). Genes associated with inflammatory pathways have been shown to be induced in mouse brain by MPTP (Grunblatt, et al. (2001); Mandel, et al. (2000)). Higher levels of proinflammatory cytokines are found in Parkinson's disease patients' brains, including IL-8 (Zhang et al, 2008), and inflammation is thought to be a major contributor to the neurodegeneration in the Parkinson's disease patients (Tansey et al, 2007). Drugs suppressing IL-8 secretion should therefore be useful in treating Parkinson's disease.

Stroke, a localized ischemic trauma to the brain, significantly increases levels of IL-8 and other related factors in the cerebrospinal fluid. IL-8 levels increase immediately following stroke, and peak on day 2 (Tarkowski, et al. 1997). At follow-up after 20 to 31 days, numbers of IL-8 mRNA expressing peripheral blood mononuclear cells were lower than during the acute stage (P<0.001), but only IL-1B and IL-17 mRNA expression had returned to the level of the healthy individuals. Numbers of MIP-1 mRNA expressing peripheral blood mononuclear cells did not differ between patients with ischemic stroke and healthy individuals at any point in time. A positive correlation was observed between numbers of IL-1Beta, IL-8, and IL-17 mRNA expressing peripheral blood mononuclear cells and the degree of neurological impairment as measured by the Scandinavian Stroke Scale 1 to 3 days after onset of symptoms (r=0.5; P<0.01 for all correlations) (Kostulas et al., 1999).

Higher levels of IL-8 in the CSF are observed following white matter strokes than grey matter strokes. Kostulas. et al. (1999) report that following stroke, IL-8 mRNA levels in peripheral blood neutrophils remain increased for up to 30 days following stroke, while other cytokines return to normal. In animal models of stroke, intracysternal administration of blocking antibodies to IL-8 are found to prevent cerebral reperfusion injury, and endotoxemia-induced acute respiratory distress syndrome (ARDS)-like lung injury (Matsumoto, et al. (1997a); Mukaida, et al. (1998)). An intracysternal neutralizing IL-8 antibody has also been reported to reduce brain edema and infarct size in rabbit brain following experimental transient focal ischemia (Matsumoto, et al. (1997b)). We interpret these data to indicate that drugs with antibody-like capacities to lower brain levels of IL-8 might be useful in the treatment and possible prevention of stroke.

Increases in the levels of IL-8 and other proinflammatory cytokines also occur in cases of traumatic brain injury (Ott, et al. (1994)). Maximal IL-8 values in cerebrospinal fluid correlate with a severe dysfunction of the blood-brain barrier. In children with severe head injuries there is a significant association between survival after traumatic brain injury and lower levels of IL-8 in the cerebrospinal fluid (CSF) (Whalen, et al. (2000); see also Sherwood, et al. (2000)). As summarized by Ott, et al. (1994), IL-8 and related agents play a central role in the cellular cascade of injury, both centrally and peripherally by inducing fever, neutrophilia, muscle breakdown, altered amino acid metabolism, depression of serum zinc levels, production of hepatic acute phase reactants, increased endothelial permeability and expression of endothelial adhesion molecules. Ott, et al. (1994) also emphasize that specific failures of gut, liver and lung have been identified due to IL-8 and other brain-derived cytokines such as IL-1, IL-6, and TNFa. Kossmann et al. (1997) and Maier, et al. (2001) have validated the brain origin of circulating IL-8, as well as IL-1 and IL-6. They demonstrate that following brain trauma these interleukins are higher in cerebrospinal fluid (CSF) than plasma. Maximal values in IL-8 in CSF are also associated with destruction of the blood brain barrier (Kossmann et al. (1997); Maier, et al. (2001)). While there appears to be a role for IL-8 in stimulating repair in the brain by the Neuronal Growth Factor (NGF) pathway (Kossmann, et al. (1997);

Sherwood, et al. (2000)), the massively elevated IL-8 levels seen in traumatic brain injury appear to exert a strong, contrary pathophysiological connection to adverse consequences of traumatic brain injury. We therefore interpret these data to suggest that drugs capable of suppressing production of IL-8 should be useful in reducing morbidity and mortality following traumatic brain injury, thereby permitting the occurrence of any positive reparative actions of low levels of IL-8.

Cardiopulmonary bypass operations are associated with a transient rise in circulating IL-8 and other cytokines in the brain (Mandate, et al. (1999)). Brain dysfunction following the operation occurs in a portion of the patients, and the mechanism may involve activation of inflammatory processes in the brain. In support of this hypothesis, Nandate, et al. (1999) show that during and following the bypass operation, IL-8 levels are consistently higher in the jugular bulb, containing blood coming from the brain to the heart, than in the paired arterial samples. Thus, specific and significant IL-8 production could be found to be produced in the cerebrovascular bed during and following the operation. The authors also report that at least one intervention, hypothermia, suppresses the changes. Thus, drugs that interfere with IL-8 production should be useful in ameliorating morbidity and mortality associated with cardiopulmonary bypass operations. Hypoxia induced by ischemia also leads to an increase in levels of intracellular adhesion molecule (ICAM)-5. (Guo, 2000). Drugs that interfere with ICAM-5 levels may also be useful in preventing brain damage following cardiopulmonary events.

Huntington's disease is a model for poly-glutamine expansion diseases, including spinocerebeller muscular atrophy, dento-rubro-pallido luysian atrophy, and other forms of spino-cerebellar atrophy. Quantitative Polymerase Chain Reaction (Q-PCR) was used to measure neuroinflammation-associated mediators in different parts of the brains of patients who had died from Huntington's disease (Silvestroni et al., 2009). In the striatum, a brain region principally affected by this disease, several key proinflammatory mediators were detected. IL-8 is specifically upregulated in the cortex and the cerebellum.

5. Viral Diseases

HIV-1 infection of macrophages results in elevation of IL-8 synthesis and secretion of IL-8 by the infected cells. Conversely, IL-8 itself stimulates HIV-1 replication in macrophages and T-lymphocytes (Lane, et al. (2001)). Consistently, Lane, et al. (2001) show that increased levels of IL-8 are present in the lymphoid tissue of patients with AIDS. Compounds which block IL-8 receptors also inhibit HIV-1 replication in both T lymphocytes and macrophages. Thus, drugs that are able to interfere with IL-8 secretion might be useful as therapeutics for HIV-1 infection, and AIDS.

HIV-1 infected patients often develop neurological disorders and HIV-1-associated dementia following invasion of the brain by activated T cells and infected macrophages. Kutsch, et al. (2000) show that the HIV-1 Tat (72aa) peptide potently induces IL-8 and related cytokines in astrocytes. IL-8 message is seen within an hour, and IL-8 protein is produced. Given the fact that IL-8 potentiates HIV-1 infection, it follows that drugs that are able to interfere with IL-8 secretion might be useful in preventing or suppressing HIV-1 infections in the CNS leading to HIV-1-associated dementia.

Figure 1:
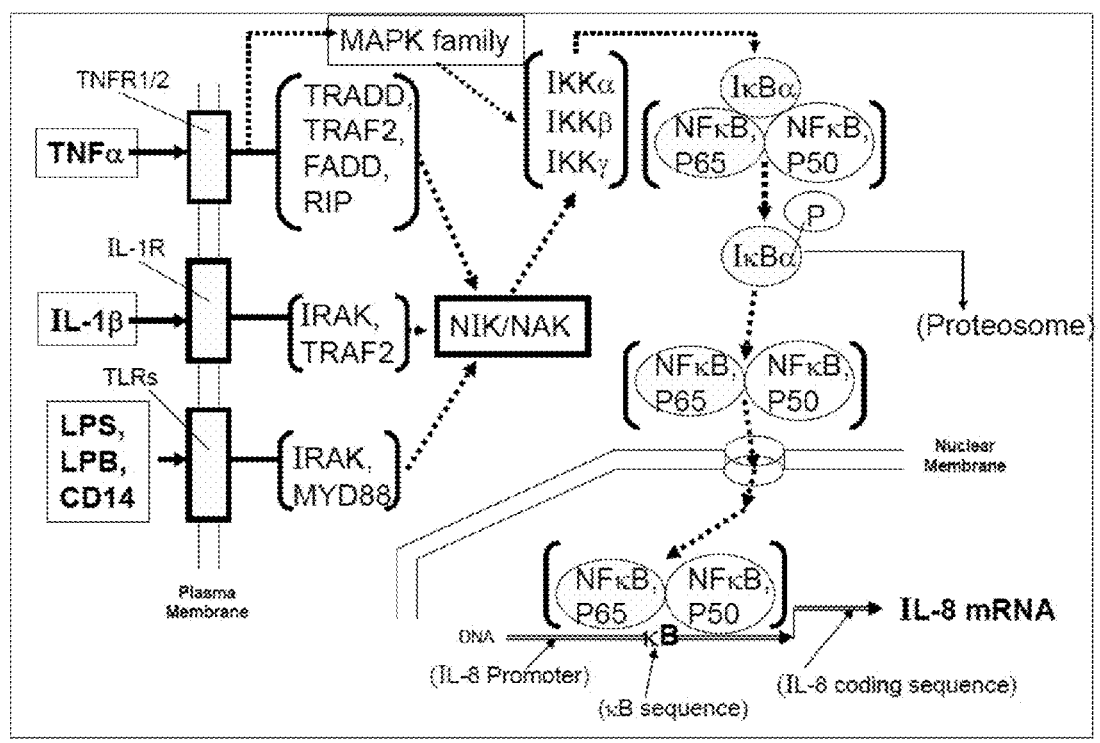
FIG. 1 illustrates the NFKB activation pathway leading to synthesis of IL-8. NFKB activation can be elicited by TNFa, IL-1b and various Toll-like Receptors (TLRs) on the plasma membrane. Following phosphorylation of IkBa, the NFKB complex enters the nucleus and finds the kB sequence on the IL-8 promoter.
Figure 2:
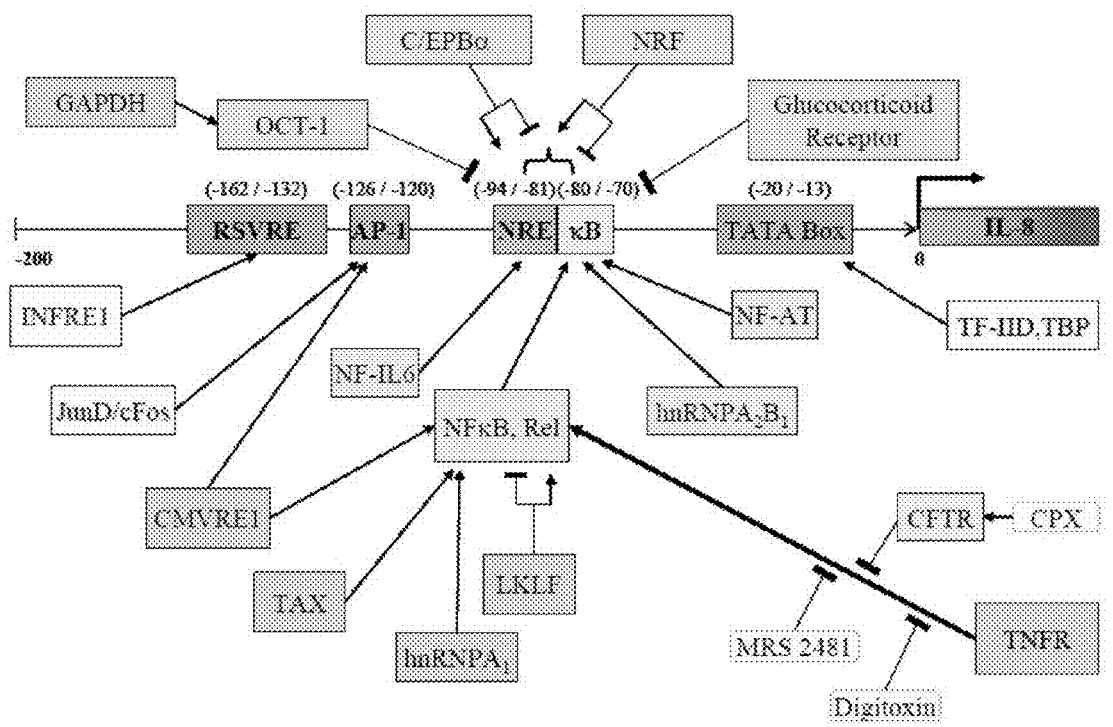
FIG. 2 illustrates the transcription factors that regulate the activation of IL-8 promoter by NFKB and other cis acting transcription factors. In addition to NFKB, multiple other factors combine to regulate IL-8 expression.

Other viral agents have an impact, either directly or indirectly, on IL-8 production by target cells. In the case of adenovirus (Gilmour, et al. (2001)), the adenoviral gene product E1A primes alveolar epithelial cells to produce elevated levels of IL-8 when exposed to environmental particulate matter that are less than 10 microns in diameter [e.g., PM (10) or hydrogen peroxide (H202)]. In the case of the human rhinovirus (HRV14; Subauste. et al. (2001)), the growth factors TNFa and epidermal growth Factor (EGF) induce the cells to both synthesize increased levels of IL-8 and to support increased viral replication in a line of human bronchial epithelial cells. In the case of respiratory syncytial virus (RSV), there is a well known responsive element for RSV on the IL-8 promoter (viz, the RSVRE) which supports a vastly increased level of IL-8 production upon RSV infection (see FIG. 2)). The viral literature is extensive on this point, and so we can only conclude that drugs able to interfere with production of IL-8 during viral infection should have the capacity either to interfere with some viral infections, or to suppress associated inflammatory symptoms.

6. Transplantation

Successful transplant surgery of kidneys, lungs and other organs depends upon high quality donor organs that tend not to be rejected by the recipient. Inflammation in the donor organ, as evidenced by high IL-8 levels, is associated with increased likelihood of graft rejection by the recipient (Zivna, et al. (1999)) and that increased serum and urine IL-8 concentrations in recipients 24 hours after kidney transplant are predictive of future rejection episodes.

In the case of lung transplants, an increased level of IL-8 in the donor bronchoalveolar lavage (BAL) fluid is associated with severe early graft dysfunction and early recipient mortality (Fisher, et al. (2001)). Fisher, et al. (2001) suggest that severe trauma patients, the frequent source of lungs for transplant, often have increased levels of IL-8, as well as neutrophils that are attracted by IL-8, increasing the likelihood that the transplant will be rejected. It is therefore possible that inclusion of digitoxin or other cardiac glycoside in the protocol, might enhance the possibility of successful transplantation.

7. Heart

The data indicate that digitoxin (II) inhibits IL-8 at a much lower concentration than is needed for digitoxin to provide therapy for cardiac contractility (see Table 2). For example, the K50 (IC50, inhibitory dose of cardiac glycoside that reduces IL-8 secretion by 50%)) for digitoxin (II) indicates that it is ca. 30-fold more potent as a CF IL-8 inhibitor than its potency as a therapeutic for cardiac failure (Srivastava et al, PNAS 2004). Specifically, while the K50 for CF IL-8 inhibition by digitoxin is ca. 0.9 nM, the toxicity-limited therapeutic concentration in the circulation of patients with heart failure is as high as ca. 37 nM. By contrast, digoxin (III), a highly potent cardiotonic drug, is ca 33-fold less potent than digitoxin (II) as a CF IL-8 suppressor. Specifically, while the K50 of digoxin for CF IL-8 inhibition is ca. 27 nM, the therapeutic concentration of digoxin in the circulation for heart failure is ca. 2 nM. The critical difference between the potent digitoxin and the relatively impotent digoxin is a hydrogen (—H) at position 12 for digitoxin (II) and a hydroxyl (—OH) at position 12 for digoxin (III) (see Table 3)). Considering the pharmacology of the entire series, it appears that the suppressive actions of cardiac glycosides on IL-8 secretion, and the classical positive actions on cardiac contractility, are mediated by completely separate mechanisms.

Patients arriving in hospital emergency rooms after suffering cardiopulmonary arrest (CPA) also have increased levels of serum IL-8 and TNFalpha. These levels peak within 12 hours post-arrest, or within 6 hours after return of spontaneous circulation (ROSC) (Ito, et al. (2001)). Patients with significantly higher levels of IL-8 tend to die or become brain dead within one week of return of spontaneous circulation. (Ito, et al. (2001)). Excessive administration of epinephrine, sometimes occurring during cardiopulmonary resuscitation, is also associated with significantly elevated of IL-8 following return of spontaneous circulation. The source of the IL-8 in the serum is not specified. However, considering the data of Nandate, et al. (1999), a central origin could be suspected. Whatever the source, it is likely that drugs that interfere with IL-8 production following return of spontaneous circulation (ROSC) might be useful in ameliorating morbidity and mortality associated with cardiopulmonary arrest.

Cardiopulmonary bypass operations are associated with a transient rise in circulating IL-8 and other cytokines (Nandate, et al. (1999)). Brain dysfunction following these operations occurs in a portion of patients, and the mechanism may involve activation of inflammatory processes in the brain. Drabe et al. (2001) have pursued genetic components associated with increased IL-8 production during cardiopulmonary bypass operations. The apolipoprotein E4 allele is historically associated with increased propensity to atherosclerosis, higher levels of lipoprotein (a) and early Alzheimer's disease. Patients carrying the apolipoprotein E4 allele have higher baseline levels of IL-8 and TNFa than patients lacking this allele. Following cardiopulmonary bypass, the apolipoprotein E4 patients, comprising 27% of the patient cohort, also have increased release of both IL-8 and TNFa, compared to patients lacking this allele. It is therefore suggested that patients with the E4 genotype should have additional perioperative therapy for the aberrantly increased systemic inflammatory response. Thus drugs that interfere with IL-8 production should thus be useful in ameliorating morbidity and mortality associated with cardiopulmonary bypass operations.

Inflammation processes are historically associated with the pathogenesis of atherosclerosis, and high levels of IL-8 have been found in atheromatous plaques (Wang et al. (1996)). Among the mechanisms, high IL-8 has been directly implicated, and the processes regulating IL-8 synthesis can be studied in vitro in cultures of human aortic endothelial cells. IL-8 is synthesized in these cells via multiple convergent pathways (Takata, et al. (2001)). For example, prevastatin (an inhibitor of 1,3-hydroxy-3-methylglutaryl co-enzyme A reductase) not only lowers cholesterol, but also suppresses thrombin-induced IL-8 production in these cells cultured in high glucose medium. The effect is not on baseline IL-8 levels, which are such a problem in cystic fibrosis, but on stimulated levels induced by thrombin. The mechanism involves inhibition of the thrombin-induced transition of ras from the cytosol to the plasma membrane. The consequence is suppression of activation of the ras-MAP (p44/42) kinase pathway, but not the kinase itself. Thus, drugs that specifically target IL-8 production should be useful in treating inflammatory aspects of atherosclerosis.

8. Gastrointestinal Disorders

Acute pancreatitis in humans is often associated with multi-organ dysfunction syndrome (MODS), principally affecting the lung (Bhatia. et al. (2001)). Experimental acute pancreatitis models have been studied in rabbits, in which IL-8 is elevated in serum and lung, and acute lung injury observed (Osman, et al. (1998); Osman, et al. (1999)). Infusion of an antibody against IL-8 during the acute pancreatitis challenge prevents lung damage, as evidenced by reduced neutrophil infiltration in the lung, while pancreatic necrosis and systemic release of pancreatic enzymes is unaffected (Osman. et al. (1998)). Thus suppression of IL-8 production during acute pancreatitis may be useful in suppressing MODS, particularly lung dysfunction.

9. Syndromes Following Bacterial Infections

Certain fevers, including that associated with typhoid fever (Kreuter et al, 1994), are known to be resistant to cyclooxygenase inhibitors, In addition, a type of fever caused by intracerebro-vascular injection of IL-8 falls into this category (Zampronio, et al. (1994)). These data suggest that drugs able to interfere with IL-8 secretion in brain should be useful as antipyretics for fevers resistant to cyclooxygenase inhibitors.

10. Cancer

Evidence suggests that certain CXC chemokines such as IL-8 are angiogenic. (Rottman, (1999)). Adenoviral gene therapy with antisense IL-8 has been successful in reducing growth of human bladder tumor cells growing subcutaneously in the nude mouse (Inoue, et al. (2001)). Additionally, high IL-8 expression in tumors is associated with advanced tumor stage and earlier death for ovarian cancer patients. (Merritt, et al., (2008)).

Adenoviral gene therapy with antisense to IL-8 has been successful in reducing growth of human bladder tumor cells growing subcutaneously in the nude mouse (Inoue, et al. (2001)). The injections of the adenoviral construct were directly into the body of the tumor, and only resulted in inhibition of growth rate relative to control capacity. Thus, drugs able to interfere with production of IL-8 could have the capacity either to interfere with tumor growth, development or metastases.

The amount of IL-8 and several other proinflammatory mediators is significantly higher in the serum of patients with bone sarcomas in comparison to patient with benign bone tumors (Rutkowski et al., 2003). IL-8 is induced when human osteogenic sarcoma cells are exposed to TNFa (Grigolo et al., 1999). Thus, there is a direct connection between TNFa and IL-8 in this type of tumor. The function of IL-8 in tumor cell growth includes angiogenesis. Thus, reducing the IL-8 level may suppress osteogenic tumor growth. In the case of lung cancer, Zhu et al., (2004) have reported that all non-small cell lung cancers tested produced modest or high levels of IL-8. Further, IL-8 can act as a growth factor for lung cancer cells. Proliferation of several lines of human non-small cell lung cancers could be attenuated by exposure to anti-IL-8 neutralizing antibody or to antibodies against the IIL-8 receptor CXCR1 but not the IL-8 receptor CXCR2. Circulating IL-8 in an orthotopic nude rat model of human non-small cell lung cancer is an indicator of cancer progression (Millar et al., 2008).

In the case of human head and neck squamous cell carcinoma, Bancroft et al., (2001) have shown that both IL-8 and VEGF are produced by tumor cells. The consequence is promotion of tumor angiogenesis and metastasis. They show that blockade of NFkB signaling specifically lowers IL-8 levels, but not VEGF levels. The importance of suppressing the NFkB signaling pathway in this type of tumor is further demonstrated by the finding that totally blocking NFkB with siRNA against NFkB itself is effective in killing squamous cell carcinoma cell lines. (Lun et al., 2005).

In the case of human colorectal cancer, a polymorphism in the IL-8 gene (−251T>A), that is associated with elevated expression of IL-8 protein, raises inflammation-related cancer risk in a large human population (Landi et al., 2003).

In the bladder cancer system, IL-8 is enhanced in production by NFkB signaling. In addition, metastasis of human bladder cancer is mediated by angiogenic action of IL-8 (Karashima et al. 2003). Consistently, human anti-IL-8 antibody inhibits orthotopic bladder cancer xenografts implanted in the bladder in a mouse model (Mian et al., 2003 by down regulation of matrix metalloproteases MMP2 and NFkB. (Manna and Ramesh, 2005)

Metastatic malignant melanoma is known to be resistant to decarbazine. This is believed to be due to the upregulation of IL-8 and vascular endothelial growth factor by decarbazine (Lev et al., 2003).

In an unbiased proteomic study of five ovarian cancer cell lines, Moscova et al. (2006) reported that IL-8 was among the most prolifically secreted proteins. Blockage of NFkB signaling by mutated IkBa has been found to inhibit angiogenesis and tumorigenicity of human ovarian cancer cells in a nude mouse model by suppressing IL-8 expression (Huang et al., 2000).

Many human breast cancer cell lines produce high levels of IL-8. In a study of human breast cancer xenografts in a SCID mouse model, Salcedo et al. (2002) show that co-administration of antibodies to IL-8 and EGF receptor substantially reduced metastatic effects. Administration of estradiol increased IL-8 secretion from both normal breast cells and cancer cells in vivo (Bendrick and Dabrosin, 2009).

In prostate cancer, including castration resistant prostate cancer, high levels of circulating IL-8, as well as IL-6, are associated with increased angiogenesis, invasion and metastases, and with decreased survival (Kurzrock, 2001). Thus a drug such as digitoxin, that suppresses IL-8 expression, may enhance the prognosis (see Examples 4, 5 and 6).

The human glioblastoma cell line U87 has been reported to produce IL-8 in response to CXCR4 stimulation and compounds which inhibit IL-8 production by this mechanism also suppress tumor growth and angiogenesis (Ping and Yao, 2006).

A middle aged man was diagnosed in 2003 with a clear cell renal carcinoma metastatic to the brain and spinal cord. In 2004, this patient was finally remanded to a hospice, paralyzed and in a delusional mental state. With only a few estimated days/weeks to live, the patient was administered 0.1 mg/day of digitoxin for a separate heart condition. A week later, the patient regained a clear sensorium, began reading a book, sat up in bed, and some weeks later left the hospice under his own power. This one case can be interpreted only as one interesting example of administration of digitoxin to one cancer patient, with a positive result.

11. Skin Disorders

Thermal injuries (viz., burns) are closely associated with increases in cytokines such as TNFa, IL-6 and IL-8 in the systemic circulation, normal and thermally injured skin and lung (Rodriguez, et al. (1993); Vindenes. et al. (1995)). Increased IL-8 concentrations seem to be related to burn size and to have a role in the pathophysiology of sepsis in patients with large burns. (Vindenes H. et al. (1995)). In a study done on burn patients, the mean patient plasma concentration of IL-8 at admission was about 60 times higher than that of healthy controls. Furthermore, patients with total body surface area burn of more than 40% had significantly higher IL-8 concentrations in plasma than patients with smaller burns. (Vindenes. et al. (1995)). Additionally, in patients without serious infectious complications, the IL-8 concentration fell gradually after injury, whereas in patients with complicating sepsis a second peak of IL-8 was demonstrated. (Vindenes. et al. (1995)).

Psoriasis is a disabling, proliferative skin disorder associated with systemic elevation of lymphocytes (Hoxtermann, et al. (1998)) and other evidences of aberrant cytokine production. Stoof et al. (2001), in a study of the mechanism of action of the antipsoriatic drug dimethylfumarate (DMF), found that DMF, in the range of 5-50 uM, suppresses IFNy stimulated production of IL-8 and related cytokines by human karatinocytes. The mechanism of action of DMF on IL-8 production may be via the NFkB pathway, since DMF causes nuclear accumulation of cytokine-induced NFkB/p50 in human dermal fibroblast cells (Vandermeeren, et al., 2001). These data suggest that drugs able to interfere with IL-8 secretion in dermal cells should be useful as antipsoriatic agents. These cytokines are thought to be responsible for the perpetuation of psoriatic lesions.

12. Miscellaneous

Endometriosis is a condition in which endometrial cells occupy areas outside of the uterus yet still respond to the menstrual cycle. The endometrial cells produce IL-8 and other inflammatory mediators which cause pain and inflammation, as well as fibrosis in surrounding tissues. IL-8 may play a role in the pathogenesis of endometriosis. The synthesis of IL-8 by endometrial stromal cells is further stimulated by IL-10 and TNFa (Bersinger et al., 2010). Serum IL-8 has also been shown to be elevated in endometriosis relative to patients with benign ovarian cysts. (Ohata et al., 2008). Higher levels of IL-8 occur in ectopic and eutopic endometrium cells than in normal endometrium in women without endometriosis during the menstrual cycle. (Ulukus et al., 2009).

EXAMPLES

The experimental examples below demonstrate the effectiveness of low doses of digitoxin in the inhibition of IL-8 and the inhibition of inflammation.

Example 1

Inhibition of IL-8

CF lung epithelial IB3-1 cells were cultured in serum free, gentimycin free LHC-8 medium (Biofluids, Bethesda, Md.) as previously described (Eidelman, 2001). The purity of the cardiac glycosides was confirmed by NMR and Mass Spectrometry with oleandrin (>98%) purity and the other cardiac glycosides (>95% purity). (See FIG. 4.) The cardiac glycosides (see FIG. 5) were prepared in ethanol and diluted to a final solvent concentration of 0.001%. Solubilized drugs were stored at 4° C. Crystalline drugs were stored in a desiccator at room temperature in the dark. Cells were grown to confluence and treated with 0, 0.01, 0.1, 1.0, 10, 100 or 1000 nM of either Oleandrin (Indofine Chemicals, Hillsborough, N.J.), digitoxin, digoxin, ouabain, digoxigenin, digitoxigenin, acetyl-strophanthidin, or digoxigenin 3,12 diAC (Sigma-Aldrich, St. Louis, Mo.) for 48 hours.

After 48 hours of incubation, cell supernatants were collected, centrifuged at 12,000 RPM for 15 seconds, and the supernatants were assayed for IL-8 using an ELISA kit from R & D systems (Minneapolis, Minn.). Data were normalized to cellular DNA with propidium iodide (Boehringer Mannheim, Mannheim, Germany). Samples of the supernatant were removed and assayed for IL-8 using an ELISA kit. (R& D Systems, Minneapolis, Minn.). As shown in Table 2 and FIG. 3, the IC 50 (dose for 50% inhibition) for spontaneous IL-8 secretion is approximately 2 nM for oleandrin and 0.9 nM for digitoxin. Table 10 shows the influence of digitoxin on cultured IB-3 cells from a cystic fibrosis lung.

TABLE 10

Influence of Digitoxin on Secretion of Selected Proinflammatory Mediators, From Cystic Fibrosis IB-3 Lung Epithelial Cells[1]

| Mediator | Control, % | Digitoxin, 10 nM, % of Control | Digitoxin, 30 nM, % of control |
|---|---|---|---|
| IL-8 | 100 | 2 | 0, Not detected |
| IL-6 | 100 | 3 | 0, Not detected |
| TNFalpha | 100 | 5 | 0, Not detected |
| ICAM1 | 100 | 19 | 30 |
| IL-1-beta | 100 | 50 | 50 |
| IFN-gamma | 100 | 100 | 35 |
| IP-10 | 100 | 100 | 100 |

[1]IB3-1 cells were incubated for 24 hours at 37° C. in different concentrations of digitoxin, and proinflammatory mediators measured by ELISA in culture medium.

Example 2

Inhibition of Collagen-Induced Arthritis by Digitoxin

Thirty DBA/1 mice from Jackson Laboratories were selected for this experiment. The mice were either injected with vehicle (n=15) or digitoxin (0.03 mg/kg, ip, once every day) (n=15). The injections were started one day prior to inducing collagen induced arthritis and continued for each day of the experiment. Collagen induced arthritis (CIA) was induced by intradermal primary immunization with 100 pg/mouse bovine CII (Chondrex, Redmond, Wash.) emulsified in complete Freund's adjuvant containing 250 mg/mouse heat-killed *Mycobacterium tuberculosis* H37Ra (BD Franklin Lakes, N.J.). Twenty-one days later, the mice were boosted by subcutaneous injection at the base of the tail with 100 pg/mouse bovine CII emulsified in complete Freund's adjuvant. Mice were scored for arthritis using the following visual scoring system: grade 0, no swelling or erythema; grade 1, mild swelling and erythema or digit inflammation; grade 2, moderate swelling and erythema confined distal to the mid-paw; grade 3, more pronounced swelling and erythema with extension to the ankle; grade 4, severe swelling, erythema, and joint rigidity of the ankle, foot, and digits. Each limb was graded with a score of 0-4, with a maximum possible score of 16 for each individual mouse. Paw thickness was determined by measuring the thickness of the most severely affected hind paw with 0- to 10-mm calipers. (Paniagua et al., J. Clin. Inv. 116:26332642, 2006). Development of pathology was followed for 48 days.

Figure 6A:
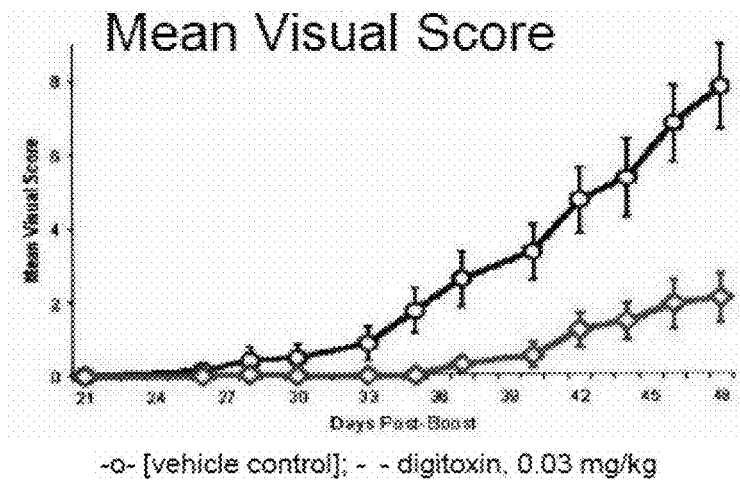
FIGS. 6A through 6C show the influence of digitoxin (0.03 mg/kg; 30 micrograms/kg) on development of collagen induced arthritis (CIA) including in FIG. 6A the mean visual score, in FIG. 6B the mean paw thickness, and in FIG. 6C the incidence of CIA in vehicle and digitoxin treated mice. Differences between vehicle and treated parameters were significant (p<0.05) at the $48^{th}$ day for all parameters.
Figure 6B:
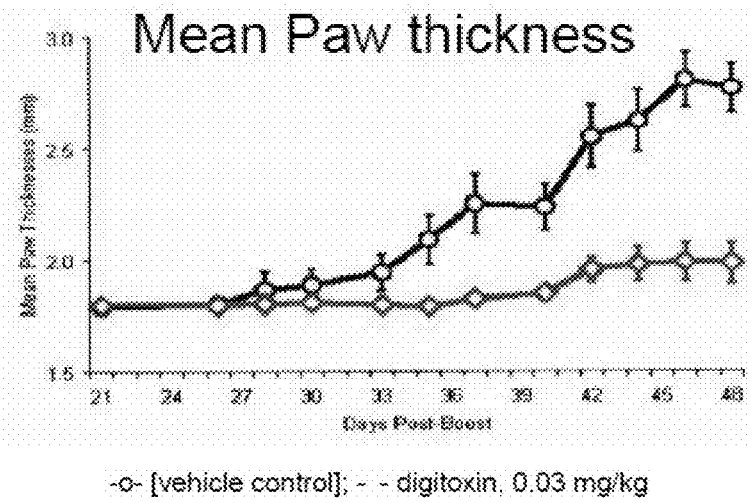
Figure 6C:
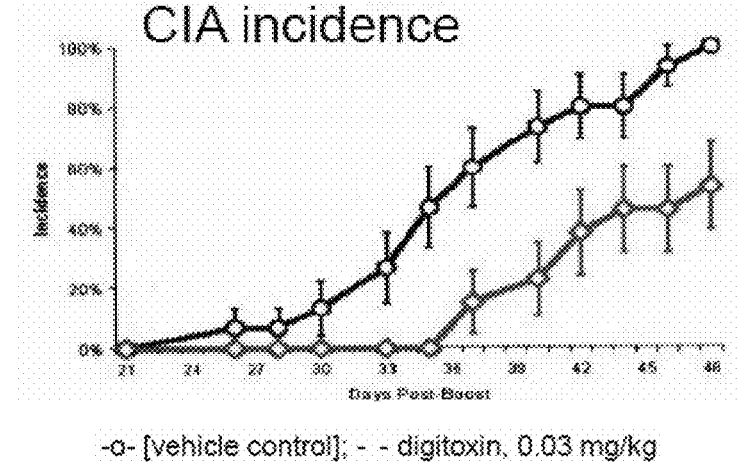

As can be seen in FIG. 6, there was significant reduction in the severity of CIA in mice treated with digitoxin. The mean paw thickness of each mouse was also decreased in mice treated with digitoxin (FIG. 6B) and the actual incidence of CIA in each mouse was determined (FIGS. 6A and C). As can be seen in FIGS. 6A and C, 100% of the vehicle treated mice developed CIA while only 50% of the digitoxin-treated mice developed symptoms to any degree.

Figure 7A:
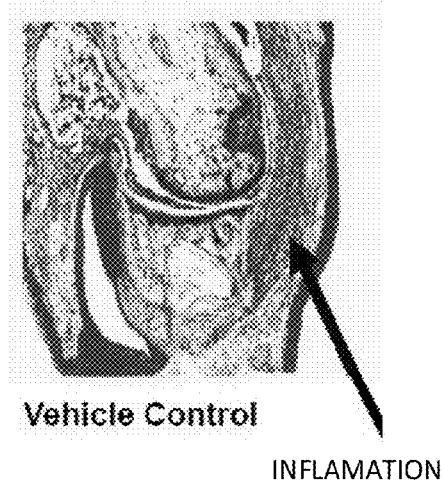
FIGS. 7A and 7B show the histopathology of metatarsal phalangeal joints taken from the hind paw of vehicle treated mice (FIG. 7A) and digitoxin (0.03 mg/kg; 30 μg/kg intraperitoneal (IP) qd) treated joints (FIG. 7B) of collagen induced arthritis mice.
Figure 7B:
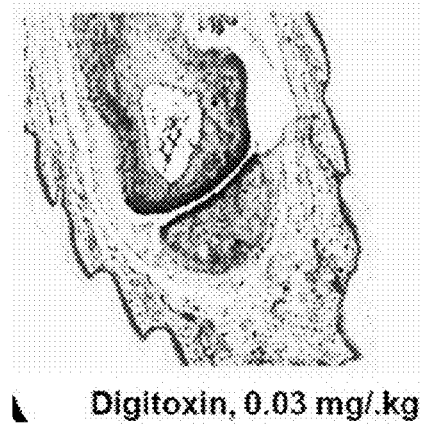
Figure 8A:
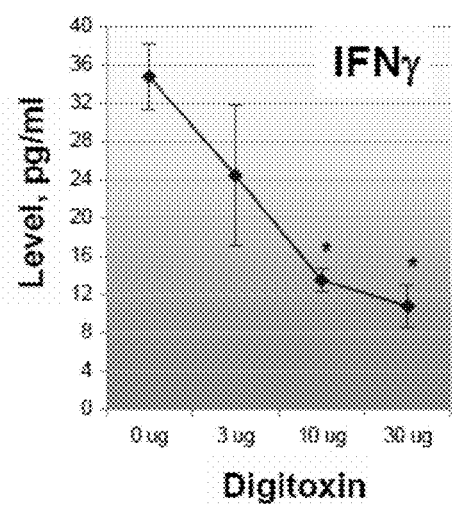
FIGS. 8A through 8H depict the inhibition of Cytokine and Chemokine production by digitoxin in a rodent model, and show, respectively, the influence of digitoxin on the expression of eight cytokines in rat lungs infected with influenza.
Figure 8B:
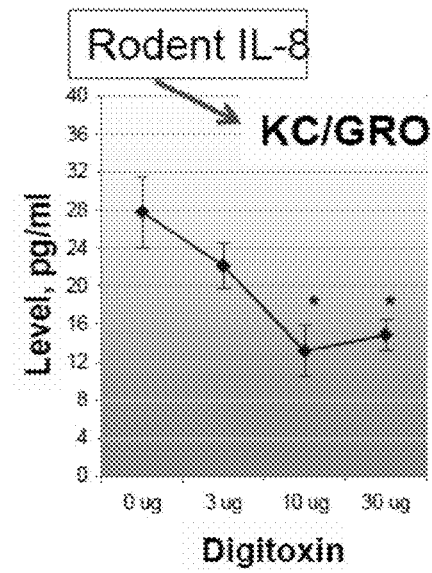
Figure 8C:
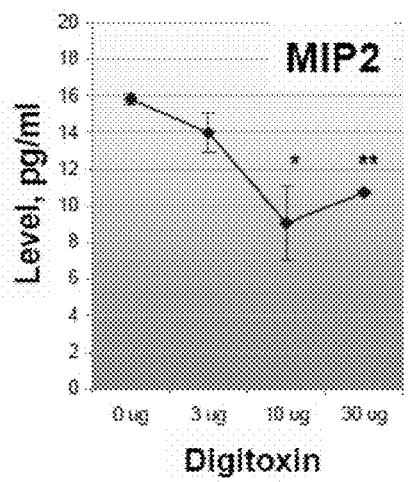
Figure 8D:
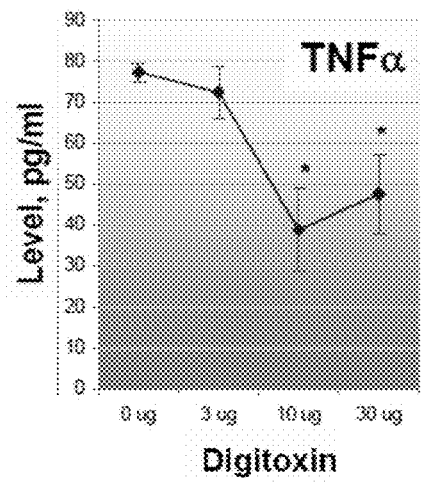
Figure 8E:
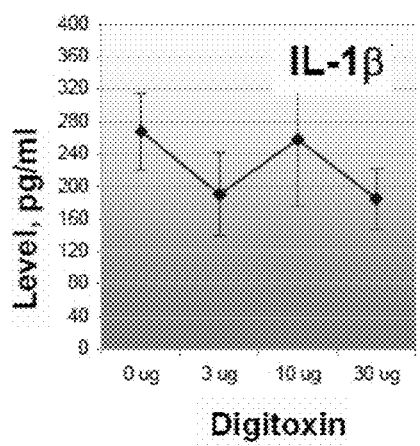
Figure 8F:
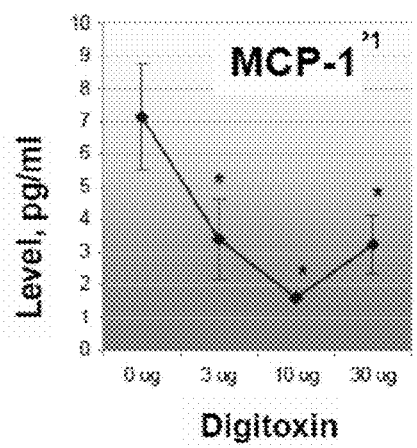
Figure 8G:
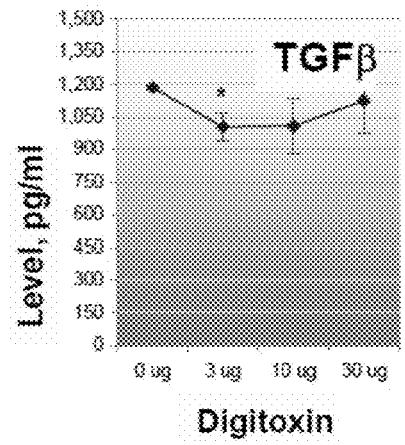
Figure 8H:
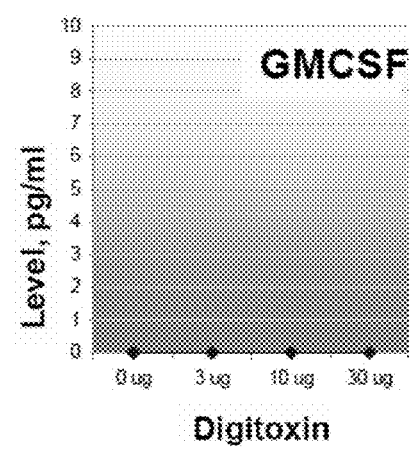

FIG. 7 shows representative samples of histopathology of metatarsal-phalangeal joints from vehicle-treated CIA mice compared with CIA mice treated with 0.03 mg/kg digitoxin. The massive focus of inflammation in vehicle treated mice (FIG. 7A) resembles the pannus tissue characteristic of rheumatoid arthritis in humans. This inflammatory focus is absent in digitoxin-treated mice (FIG. 7B) demonstrating that digitoxin blocks formation of pannus-like proinflammatory pathology in the CIA mouse. These data show that digitoxin can induce a profound reduction in an experimental model of inflammation.

Example 3

Inhibition of Pro-Inflammatory Cytokines and Chemokines in the Rodent Lung by Digitoxin Fifteen standard cotton rats were divided into five groups of three each. Inflammation was induced to further investigate the action of digitoxin on lung inflammation. The rats in the treatment groups were pre-treated on the preceding day with either 3, 10, or 30 micro-g/kg intraperitoneally. The injection of digitoxin was given each day for 4 days. Each rat was then treated on Day 1 with 100 microliters of Wuhan Strain influenza virus (titer-$10^8$ TC-IC 50/ml) (IC is Inhibitory Concentration) by intra-nasal administration to induce lung inflammation.

Mice received injections according to the following protocol: Group A: digitoxin, 3 microgram/kilo/rat in 200 microliters PBS 12 hours before infection; then every day thereafter at 9:30 AM for 4 days. The rats were sacrificed on the last day 4 hrs after treatment.

Group B: digitoxin, 10 microgram/kilo/rat in 200 microliters PBS, 12 hours before infection; then every day thereafter at 9:30 AM for 4 days. The rats were sacrificed on the last day 4 hrs after treatment.

Group C: digitoxin, 30 microgram/kilo/rat in 200 microliters PBS, 12 hours before infection; then every day thereafter at 9:30 AM for 4 days. The rats were sacrificed on the last day 4 hrs after treatment.

Group D (control): No digitoxin, but treated with 100 microliter influenza; sacrificed on Day 1.

Group E (control): No digitoxin, but treated with 100 microliter influenza; sacrificed on Day 4.

Pieces of lung were harvested on day 4 and homogenized in PBS by glass-on-glass homogenizer in 1 gram/ml. Samples are frozen on dry ice, and then transferred to −80° C. for analysis. Lung tissue was assayed using commercial micro-sandwich ELISA assays (Allied Biotech, Ijamsville, Md.; Searchlight System, Pierce-Thermo, Rockford, Ill.) in terms of pg/ml to determine the effect of digitoxin on IFNgamma, GRO/KC, MIP-2, TNFα, IL-1 beta, MCP-1, TGF-beta and GM-CSF. Rodents lack IL-8 and instead have GRO/KC and MIP-2. As shown in FIG. 8, there were significant reductions of GRO/KC, MIP-2, IFNγ, TNFα and MCP-1. No significant changes were seen for IL-13, and TGFβ. GM-CSF was undetectable in the tissue under any conditions.

These data show that in vivo digitoxin can induce a profound, dose-dependent reduction in an experimental model of lung inflammation in a rodent model. As anticipated, GRO/KC and MIP-2, the rodent equivalent of IL-8 were suppressed by digitoxin. Certain other proinflammatory analytes were also reduced, including TNFα. This alternative model therefore represents a second, positive test of the anti-inflammatory power of low doses of digitoxin in vivo.

Example 4

Cardiac Glycoside-Induced Cancer Cell Death

HeLa cervical cancer cells obtained from the ATCC (Manassas, Va.) were cultured in Dulbecco's modified Eagle's medium, supplemented with 10% fetal bovine serum, 2 mM glutamine, penicillin (100 U/ml), and streptomycin (100 mg/ml). The cells were incubated for 24 hours with 10, 30, 50, 70 or 100 nM of oleandrin, 50, 70, 100, 300, 500 or 700 nM of digitoxin, or 25, 50, 100, 300, 500, or 1000 nM of ouabain in a total volume of 1.0 ml. Culture medium from incubated cells supernatant solution was collected and microfuged for 30 seconds at 12,000 RPM. The supernatant solution was collected from the cell pellet and combined with 100 microliters of culture medium to triplicate wells in a 96 well flat bottom culture plate. The cells lysed with 2% triton X100 were included as a cell Lactate Dehydrogenase (LDH) total control. 100 microliters of culture medium was included as a blank control. 100 microliters of reaction mixture (Diaphorase, NAD+ and iodotetrazolium chloride (INT) and NaLactate) was then added to each well and the mixture was incubated at room temperature for 30 minutes. Absorbance was measured at 490 nm and the percent cytotoxicity as the fraction of LDH released from the cell by the test substance was calculated.

Figure 9A:
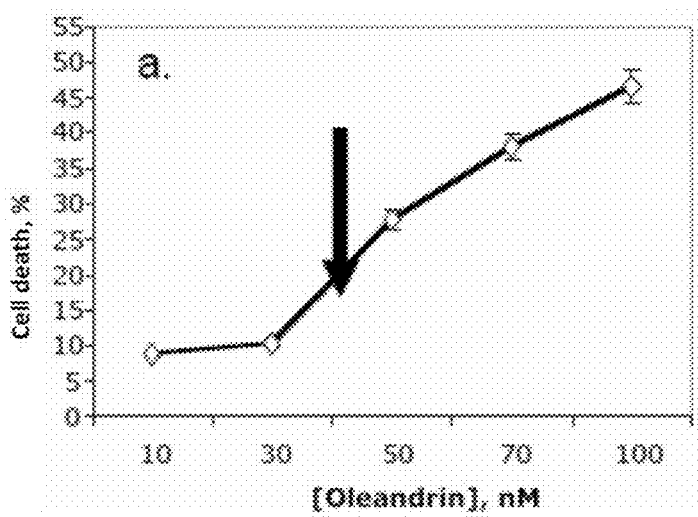
FIG. 9A shows the cell death curve of HeLa cells treated with increasing concentrations of oleandrin, with an arrow indicating the threshold concentration of the onset of cell death.
Figure 9B:
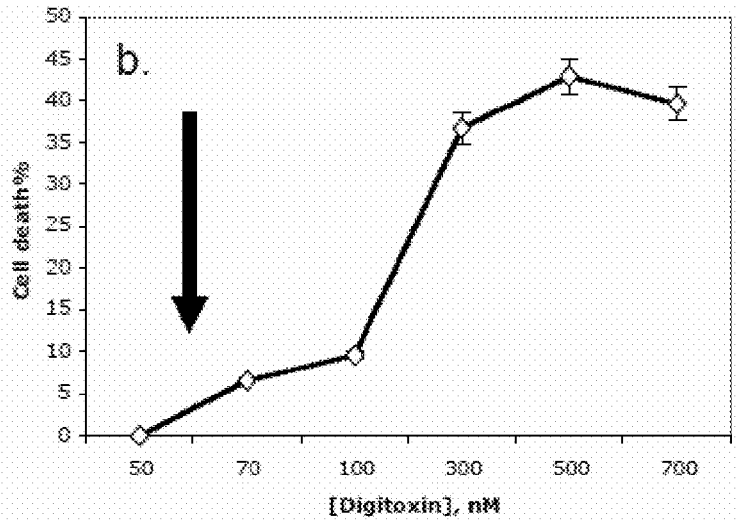
FIG. 9B shows the cell death curve of HeLa cells treated with increasing concentrations of digitoxin, with an arrow indicating the threshold concentration of the onset of cell death.
Figure 9C:
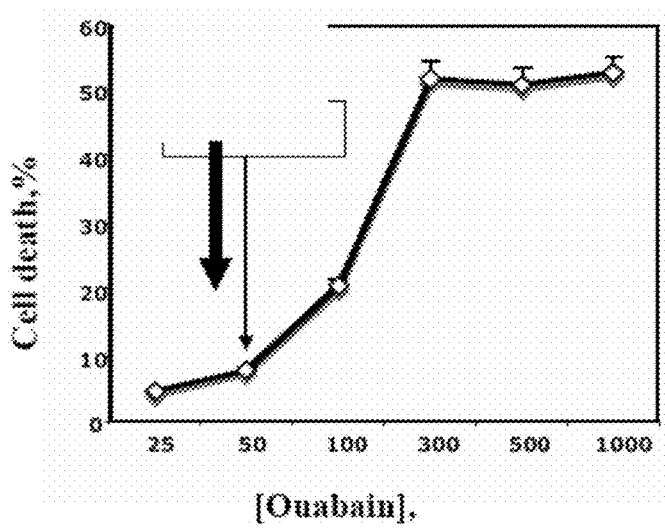
FIG. 9C shows the cell death curve of HeLa cells treated with increasing concentrations of ouabain, with an arrow indicating the threshold concentration of the onset of cell death.

As shown in FIG. 9, the threshold for an increase in cell death, in vitro, occurs at drug concentration of ca. 30 nM for oleandrin, ca. 50 nM of ouabain, and ca. 70-100 nM for digitoxin. IC50 doses for these drugs are ca. 100 nM for oleandrin and ca. 200 nM for digitoxin and ouabain. By comparison, in studies with human umbilical vein endothelial cells (HUVEC), a 50% kill concentration for ouabain was found to be 240 nM (Qiu et al, 2008a), and 357 nM (Ark et al, 2010), respectively (See Table 2).

Example 5

Suppression of Castration-Resistant Prostate Cancer Cell Growth and Metastases in Rats, In Vivo and In Vitro; and in Human PC3 Cells In Vitro by Cardiac Glycoside Experiment #1:

Thirty Lobund-Wistar rats were implanted subcutaneously in the flank with $1 \times 10^6$ syngeneic PAIII Castration Resistant Prostate Cancer cells. After 10 days, fifteen rats were treated for the next 30 days with digitoxin at a dose of 0.03 mg/kg (calculated as a concentration of 39 nM in terms of distribution into total body water). On day 40, the primary subcutaneous tumors were removed and weighed. Metastases to the pleural surfaces of the lungs were counted and their diameters measured.

As shown in Table 4, which illustrates the influence of digitoxin on sub-cutaneous primary PAIII cell tumor growth and size and number of pleural metastases in a rat model of castration-resistant prostate cancer. The rats were treated with digitoxin (0.03 mg/kg) for 30 days. Both the weight of the primary tumor, and the number of metastases and the size of each metastasis were significantly reduced.

TABLE 4

Influence of Digitoxin on Sub-Cutaneous Primary PAIII Tumor Growth, and Size and Number of Pleural Metastases

| Treatment[3] | Weight of Primary Tumor, gm (median) | Number of Pleural Metastases (median) | Diameter of metastasis, mm (median) |
|---|---|---|---|
| Control | 24.8 | 28 | 1.15 |
| Digitoxin[2] | 19.6 | 16 | 0.87 |
| Mann-Whitney[1] | P = 2E−04 | P = 0.009 | P = 0.004 |

[1]Two-tailed t test
[2]Concentration of Digitoxin = ca. 1.75 nM
[3]Experiment: 10⁶ PAIII cells were injected sub-cutaneously into LW rats; 10 days later, daily injections of digitoxin (0.03 mg/kg) were initiated for 30 days.

In addition, as shown in Table 5, the influence of digitoxin on levels of IL-6 and CINC1 (name for IL-8 equivalent in the rat) in the serum of rats bearing PAIII tumors, levels of both proinflammatory mediators IL-6 and IL-8 were significantly reduced.

TABLE 5

Reduction of Serum IL-6 and CINC1(KC, IL-8) by Digitoxin in Rats Bearing PAIII Primary Tumors and Pleural Metastases

| Treatment | Interleukin-6 (IL-6) pg/ml | CINC1/KC (rat IL-8 equivalent) pg/ml |
|---|---|---|
| Control | 47.9 ± 14.1 | 60.32 ± 20.6 |
| Digitoxin | 37.0 ± 16.9 | 47.9 ± 14.4 |
| Mann-Whitney[1] | P = 0.006 | P = 0.03 |

[1]Median, Two-tailed t test
2. Measured concentration of Digitoxin in serum = ca. 1.75 nM
3. Experiment: 10⁶ PAIII cells were injected sub-cutaneously into LW rats; 10 days later, daily injections of digitoxin (0.03 mg/kg) were initiated for 30 days. Serum was collected on day 30.

Experiment #2:

Thirty Lobund-Wistar rats were injected intravenously with one million PAIII cancer cells. Simultaneously, half the rats were also injected with digitoxin (0.03 mg/kg), and injected with the amount of digitoxin every day for ten days. On the tenth day, the animals were sacrificed, and the size and number of metastatic foci in the lung pleura measured.

Results:

As shown in Table 6, which illustrates the influence of digitoxin on implantation of growth of pleural metastases following intravenous administration of PAIII cancer cells in the rat, the number of metastases is unaffected, but the size of each metastatic site is significantly reduced. The number of metastatic sites was independent of digitoxin treatment, but the size of each metastatic focus was significantly reduced in the digitoxin-treated rats.

TABLE 6

Influence of Digitoxin on Implantation and Growth of Pleural Metastases, Following Intravenous PAIII Cancer Cell Administration

| Treatment[3] | Number of pleural metastatic foci (median) | Diameter of metastatic foci, mm, (median) |
|---|---|---|
| Control | 129 | 2.07 |
| Digitoxin[2] | 122 | 1.76 |
| Mann-Whitney[1] | P = 0.492 | P = 0.003 |

[1]Median, Two-tailed t test
[2]Concentration of Digitoxin = ca. 1.75 nM
[3]Experiment: 10⁶ PAIII cells were injected I.V. into LW rats, simultaneously with daily injection of digitoxin (0.03 mg/kg) for 10 days.

Experiment #3:

PAIII cancer cells were placed into culture, and allowed to grow to ca. 80% confluence. The cells were then treated with 6 nM digitoxin for 24 hours, and analyzed for changes in microRNAs and mRNAs.

Results for MicroRNAs:

As indicated in Table 7, digitoxin treatment of rat PAIII castration-resistant prostate cancer cells in tumors results in the significant change in expression of specific microRNAs. The most profoundly elevated microRNA is MicroRNA 376a. The effect of digitoxin was to elevate the expression of two microRNAs, miR 376a and miR-670, and to reduce expression of eight. Elevation of a microRNA causes the target mRNAs to be reduced. These data also suggest that the miRNAs, such as these but not limited to these miRNAs, that are associated with production of metastases may be useful as supplements to digitoxin or as medicaments to supplement other treatment modalities such as other cancer therapies, or on their own independent of digitoxin or any other therapeutic agent.

Table 7

MicroRNAs Changed by Exposure of Rat PAIII Tumor Cells to Digitoxin

TABLE 7

MicroRNAs Changed by Exposure of rat PAIII Cells in Tumors to Digitoxin[1,2]

| microRNA | DDCt, Digitoxin − Control | Fold Change[3,*] |
|---|---|---|
| miR-98 | 11.005 | 4.86E−04↓ |
| miR-291a-3p | 19.13 | 1.74E−06↓ |
| miR-346 | 16.57 | 1.02E−05↓ |
| miR-421 | 4.61 | 0.041↓ |
| miR-667 | 7.01 | 0.0078↓ |
| miR-670 | −12.11(↑) | 4,437.6↑ |
| miR-879 | 11.31 | 3.9E−04↓ |
| miR-347 | 4.34 | 0.049↓ |
| miR-376a | −32.75(↑) | 7.20E+9↑ |
| miR488 | 20.10 | 8.92E−07↓ |

[1]Experiment: Cells treated with 6 nM Digitoxin, for 24 hours.
[2]Method: Based on DDct_Drug-Vehicle method; TaqMan
[3]Statistics: 3 independent cultures treated with vehicle vs 3 independent cultures treated with digitoxin.
*= $P < 0.05$.
↑ = Increased by digitoxin;
↓ = reduced by digitoxin.

Table 8 illustrates the fact that digitoxin reduces the expression of several messenger RNAs associated with epithelial-mesenchymal-transition (EMT) in rat PAIII castration resistant prostate cancer tumors. EMT gene expression is associated with potential for growth and metastasis of epithelial tumors. As shown in Table 8, four Epithelial-Mesenchymal-Transition (EMT) genes were detected. These included Vimentin, Hepatocyte Growth Factor (HGF), FoxP3, and Zeb2. Table 8 shows that these 4 were found to be significantly reduced in rat PAIII cells, when treated with 0.03 mg/kg digitoxin for 30 days in vivo. These data suggest that the trend in low dose digitoxin treated rat prostate cancer cells is to suppress the EMT process. These data also suggest that the miRNAs associated with production of these mRNAs may be useful as supplements to digitoxin or as medicaments on their own, independent of digitoxin.

TABLE 8

Effect of Digitoxin on Expression of Detected Epithelial-Mesenchymal-Transition (EMT) mRNAs in vivo in Rat PAIII Tumors

| EMT mRNA | Ratio (FPKM): digitoxin/control; (% change) |
|---|---|
| Vimentin | ↓ 0.9, (−10%) |
| FOXP3 | ↓ 1.3, (−30%) |
| Zeb2 | ↓ 1.3, (−30%) |
| Hepatocyte Growth Factor | ↓ 2.0, (−50%) |

Example 6

Suppression of Epithelial-Mesenchymal-Transition in Human Castration-Resistant Prostate Cancer PC3 Cells In Vitro by Cardiac Glycoside Experiment:

Human castration-resistant prostate cancer PC3 cells were placed into culture, and allowed to grow to ca. 80% confluence. The cells were then treated with 10 and 25 nM digitoxin for 24 hours, and analyzed by Western blot for changes in Vimentin, E-Cadherin and SNAI1. These are proteins are classically associated with the Epithelial-Mesenchymal-Transition (EMT).

Results:

As shown in Table 9, E-cadherin, Vimentin and SNAI1 were all detected by standard Western blots in the cultured PC3 cell line. When incubated for 24 hours in either 10 nM or 25 nM digitoxin, the bands became undetectable meaning the proteins were all reduced. These data corroborate that low doses of digitoxin are able to suppress the EMT process in human castration-resistant prostate cancer cells.

TABLE 9

Effect of Digitoxin on Expression of Epithelial Mesenchymal Transition (EMT) Protein in Cultured Human PC3 Cells

| Protein | Vehicle Control (% Band Intensity) | Digitoxin, 10 nM (% Band Intensity) | Digitoxin, 25 nM (% Band Intensity) |
|---|---|---|---|
| E-Cadherin | 100% | 0%, undetectable | 0%, undetectable |
| Vimentin | 100% | 0%, undetectable | 0%, undetectable |
| SNAI1 | 100% | 0%, undetectable | 0%, undetectable |

[1]Experiment: PC3 Cells treated with 10 and 25 nM Digitoxin, for 24 hours, and assayed by standard Western blot analysis.

The foregoing invention has been described in detail by way of example for purposes of illustration and clarity of understanding, not for limitation, and it will be apparent to the artisan that certain changes and modifications may be practiced within the scope of the appended claims. In this context, various publications and other references have been cited within the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

REFERENCES

Abman, et al., "Early Bacteriologic, Immunologic, and Clinical Courses of Young Infants with Cystic Fibrosis Identified by Neonatal Screening", J. Pediatrics, 119, 211-217 (1991).

Aizman, O., et al., "Ouabain, a Steroid Hormone that Signals with Slow Calcium Oscillations", Proc. Nat. Acad. Sci. (USA), 98, 13420-13424 (2001).

Amin, et al, "Inflammation and Structural Changes in the Airways of Patients with Primary Sjogren's Syndrome, Respir. Med., 95, 11, 904-10 (2001).

Anderson, et al., "Generation of cAMP Activated Chloride Currents by Expression of CFTR", Science, 2516, 879-682 (1991).

Ark M, Ozdemir A, and Polat B Ouabain-induced apoptosis and Rho kinase: a novel caspase-2 cleavage site and fragment of Rock-2. *Apoptosis* 15:1494-1506, 2010.

Arispe, et al., "Alzheimer's Disease Amyloid B Protein Forms Calcium Channels in Bilayer Membranes: Blockade by Tromethamine and Aluminum, Proc. Nat. Acad. Sci. (USA), 90, 567-571 (1993).

Arispe, et al., "Direct Activation of Cystic Fibrosis Transmembrane Conductance Regulator by 8-Cyclopentyl-1,3-Dipropylxanthine and 1,3-Diallyl-8-Cyclohexylxanthine", J. Biol. Chem., 273, 5724-5734 (1998).

Arispe, et al., "Intrinsic Anion Channel Activity of the Recombinant First Nucleotide Binding Fold Domain of to Cystic Fibrosis Transmembrane Conductance Regulator Protein", Proc. Nat. Acad. Sci. (USA), 89, 1539-1543 (1992).

Arispe, et al, "Zn2+ Interaction with Alzheimer's Amyloid (3-Protein Calcium Channels", Proc. Nat. Acad. Sci. (USA), 93, 1710-1715 (1996).

Armstrong, et al., "Lower Airway Inflammation in Infants and Young Children with Cystic Fibrosis", Am. J. Respir. Crit. Care Med., 156, 1197-1204 (1997).

Avramescu C, Biciusca V, Ddianu T, Turculeanu A, Balawiu M, Popescu S N, Ionete 0, Simionescu C. Cytokine panel and histopathological aspects in the systemic lupus erythematosus. Rom J Morphol Embryol.; 51:633-640, 2010.

Bailey, et al., "Pharmacogenomics—It's Not Just Pharmacogenetics", Curr. Opin. Biotechnol., 6, 595-601 (1998).

Baldwin, et al., "The NF-KB and IxB proteins: New Discoveries and Insights", Annu. Rev. Immunol. 14, 649-681 (1996).

Bear, et al., "cAMP-Activated Chloride Conductance in the Colonic Cell Line Caco-2", AM. J. Physiol., 262, C251-C256 (1992).

Bedard, et al., "Release of Interleukin-8, Interleukin-6, and Colony-Stimulating Factors by Upper Airways Epithelial Cells: Implications for Cystic Fibrosis", Am. J. Resp. Cell Mol. Biol., 9, 455-462 (1993).

Bendrick C and Dabrosin C Estradiol increases IL-8 secretion of normal human breast tissue and breast cancer in vivo *J. Immunol.* 182:371-378, 2009.

Berger, et al., "Identification and Regulation of the Cystic Fibrosis Transmembrane Conductance Regulator-Generated Chloride Channel", J. Clin. Inv., 88, 1422-1431 (1991).

Bersinger N A, et al, "Dose-response effect of interleukin (I1)-1beta, tumor necrosis factor (TNF)-alpha, and interferon-gamma on the in vitro production of epithelial neutrophil activating peptide-78 (ENA-78), IL-8 and IL-6 by human endometrial stromal cells" *Arch. Gynecol. Obstet* 10.1007/s00404-010-1520-3, 2010.

Betz, R., et al., "Increased Sputum IL-8 and IIL-5 in Asymptomatic Airway Hyperresponsiveness", Lung, 179, 119-133 (2001).

Bhatia, et al., "Inflammatory Mediators as Therapeutic Targets in Acute Pancreatitis", Curr. Opin. Investig. Drugs, 2, 496-501 (2001).

Bonfield, et al., "Normal Bronchial Epithelial Cells Constitutively Produce the Anti-Inflammatory Cytokine Interleukin 10, which is Downregulated in Cystic Fibrosis", Am. J. Respir. Mol. Biol., 13, 257-261 (1995a).

Bonfield, et al., "Inflammatory Cytokines in Cystic Fibrosis Lungs, Am. J. Respir. Crit. Care Med., 152, 2111-2118 (1995b).

Brasier, et al., "A Promoter Recruitment Mechanism for Tumor Necrosis Factor-a-Induced Interleukin-8 Transcription in Type II Pulmonary Epithelial Cells: Dependence on Nuclear Abundance of Rel-A, NF-KB, and c-Rel Transcription Factors", J. Biol. Chem., 273, 3551-3556 (1998).

Bretscher, et al., "Regulation of Cortical Structure by the Ezrin-Radaxin-Moesin Protein Family", Curr. Opin. Cell Biol., 11, 109-116 (1999).

Briars, et al., "Faecal Interleukin-8 and Tumour Necrosis Factor-Alpha Concentrations in Cystic Fibrosis", Arch. Dis. Child, 73, 74-76 (1995).

Brockman, et al., "Coupling of a Signal Response Domain in I Kappa B Alpha to Multiple Pathways for NF-Kappa B Activation", Mol. Cell. Biol., 15, 2809-2818 (1995).

Casavola, et al., "CPX a Selective A1-Adenosine-Receptor Antagonist, Regulates Intracellular pH in Cystic Fibrosis Cells", Am. J. Physiol., 269, C226-233 (1995).

Casola, et al., "Requirement of a Novel Upstream Response Element in Respiratory Syncytial Virus-Induced IL-8 Gene Expression", J. Immunol., 164, 5944-5951 (2000).

Cheng, et al., "Defective Intracellular Transport and Processing of CFTR is the Molecular Basis of Most Cystic Fibrosis", Cell, 63, 827-834 (1990).

Cohen, et al., "CPX (1,3-Dipropyl-8-Cyclopentyl xanthine) and other Alkyl-Xanthines Differentially Bind to the Wild Type and AF508 Mutant First Nucleotide Binding Fold (NBF-1) Domains of the Cystic Fibrosis Transmembrane Conductance Regulator (CFTR)", Biochemistry, 36, 6455-6461 (1997).

Choi et al, Cellular injury and neuroinflammation in children with chronic intractable epilepsy. *J Neuroinflammation.* 6:38. doi: 10.1186/1742-2094-6-38. PMID:20021679, 2009

Collins, "Cystic Fibrosis Molecular Biology and Therapeutic Implication, Science, 256, 774-779 (1992).

Courchesne, et al., "Comparison of In-Gel and On-Membrane Digestion Methods at Low to Sub-pmol Level for Identification of Gel-Separated Proteins", Electrophoresis, 18, 369381 (1997).

Courchesne, et al., "Optimization of Capillary Chromatography Ion Trap Mass Spectrometry for Identification of Gel-Separated Proteins", Electrophoresis, 19, 956-967 (1998).

Cruse, et al., Illustrated Dictionary of Immunology. CRC Press, Boca Raton, Appendix 3 (1995).

Dean, et al., "Interleukin-8 Concentrations are Elevated in Bronchoalveolar Lavage, Sputum, And Sera of Children with Cystic Fibrosis", Pediatr. Res., 34, 159-161 (1993).

DeFranco, et al., "Macrophage Signaling in Response to Bacterial Lipopolysaccharides", Pediatric Pulm., S 19, 124 (1999).

De Herdt et al, Effects of vagus nerve stimulation on pro- and anti-inflammatory cytokine induction in patients with refractory epilepsy. *J Neuroimmunol.* 214(1-2):104-8. doi: 10.1016/j.jneuroim.2009.06.008, 2009

Denning, et al., "Localization of Cystic Fibrosis Transmembrane Conductance Regulator in Chloride Secretory Epithelia", J. Clin. Inv., 89, 339-349 (1992b).

Dignam, et al., "Accurate Transcription Initiation by RNA Polymerase II in a Soluble Extract from Isolated Mammalian Nuclei", Nucleic Acid. Res., 11, 1475-1489 (1983).

DiMango, et al., "Activation of NF-kappaB by Adherent *Pseudomonas Aeruginosa* in Normal and Cystic Fibrosis Respiratory Epithelial Cells", J. Clin. Invest., 101: 2598-2605 (1998).

Dimango, et al., "Diverse *Pseudomonas Aeruginosa* Gene Products Stimulate Respiratory Epithelial Cells to Produce Interleukin-8.", J. Clin. Invest., 96, 2204-2210 (1995).

Direskeneli H, Ozdrogen H, Korkmaz C, Akoglu T, Yazici H Serum soluble intracellular adhesion molecule 1 and interleukin 8 levels in Familial Mediterranean Fever. *J. Rheumatol.* 26: 1983-1986, 1999.

Drabe, et al., "Genetic Predisposition in Patients Undergoing Cardiopulmonary Bypass Surgery is Associated with an Increase of Inflammatory Cytokines", Eur. J. Cardiothorac. Surg., 20, 609-613 (2001).

Drumm, et al., "Chloride Conductance Expressed by DF508 and other Mutant CF IRs in *Xenopus* Oocytes", Science, 254, 1797-1799 (1991).

Dzimiri N, et al. "Influence of derivation on the lipophilicity and inhibitory actions of cardiac clycosides on myocardial Na+-K+-ATPase." *Br. J. Pharmac.* 91:31-38, 1987.

Egan, et al., "Defective Regulation of Outwardly Rectifying Cl Channels by Protein Kinase A Corrected by Insertion of CFTR", Nature, 358, 581-584 (1992).

Eidelman, et al., "A1-Adenosine-Receptor Antagonists Activate Chloride Efflux from Cystic Fibrosis Cells", Proc. Nat. Acad. Sci. (USA), 89, 5562-5566 (1992).

Eidelman, et al., "Genes from the TNFaR/NFKB Pathway Control the Pro-Inflammatory State in Cystic Fibrosis Epithelial Cells", Molecular Medicine, 7, 523-534 (2001a).

Eidelman, et al., "Role for Aberrant Phospholipid Interactions in the Trafficking Defect of AF508-Cystic Fibrosis Transmembrane Conductance Regulator (CFTR)", Biochemistry, in review (2002).

Eisen, et al., "Cluster Analysis and Display of Genome-Wide Expression Patterns", Proc. Nat. Acad. Sci. (USA), 95, 14863-14868 (1998).

Elner, et al., "Cytokines in Proliferative Diabetic Retinopathy and Proliferative Vitreoretinopathy", Curr. Eye Res., 14, 1045-1053 (1995).

Elner, et al., "Interferon-Induced Protein 10 and Interleukin 8. C—X—C Chemokines Present in Proliferative Diabetic Retinopathy", Arch. Ophthal., 116, 1597-1601 (1998).

Engelhardt, J. G., et at, "Submucosal Glands are the Predominant Site of CFTR Expression in the Human Bronchus", Nature Genetics, 2, 240-247 (1992).

Ertenli, et al., "Synovial Fluid Cytokine Levels in Behcet's Disease, Clin. Exp. Rheumatol. Suppl., 24, S37-41 (2001).

Ferrari, et al., "Pharmacogenomics: A New Approach to Individual Therapy of Hypertension?", Curr. Opin. Nephrol. Hypertens, 7: 217-221 (1998).

Fisher, et al., "Elevated Levels of Interleukin-8 in Donor Lungs is Associated with Early Graft Failure After Lung Transplantation, Am. J. Respir. Crit. Care Med., 163, 259265 (2001).

Francoeur, C., et al., "Nitric Oxide and Interleukin-8 as Inflammatory Components of Cystic Fibrosis", Inflammation, 19, 587-598 (1995).

Fried, et al., "Equilibria and Kinetics of Lac Repressor-Operator Interactions by Polyacrylamide Gel Electrophoresis, Nucleic Acid Res., 9, 6505-6510 (1981).

Fulmer, et al., "Two Cystic Fibrosis Transmembrane Conductance Regulator Mutations Have Different Effects on Both Pulmonary Phenotype and Regulation of Outwardly Rectified Chloride Currents", Proc. Nat. Acad. Sci. (USA), 92, 6832-6836 (1995).

Gabriel, et al., "CFTR and Outward Rectifying Chloride Channel are Distinct Proteins with a Regulatory Relationship", Nature, 363, 263-268 (1993).

Gales, et al., "A. DNAse Footprinting: A Simple Method for the Detection of Protein-DNA Binding Specificity", Nucleic Acid Res., 5, 3157-3170 (1978).

Gao, et al., "Inhibition of Interleukin-8 Synthesis by Intraarticular Methotrexate Therapy in Patients with Rheumatoid Arthritis", Z. Rheumatol., 57, 95-100 (1998).

Garofalo, et al., "Transcriptional Activation of the Interleukin-8 Gene by Respiratory Syncytial Virus Infection in Alveolar Epithelial Cells: Nuclear Translocation of the RelA Transcription Factor as a Mechanism Producing Airway Mucosal Inflammation", J. Virol., 70, 8773-8781. (1996).

Gibson, et al., "Heterogeneity of Airway Inflammation in Persistent Asthma: Evidence of 100 Neutrophilic Inflammation and Increased Sputum Interleukin-8, Chest, 119, 1329-1336 (2001).

Gilmour, et al., "Adenoviral El A Primes Alveolar Epithelial Cells to PM (10)-Induced Transcription of Interleukin-8, Am. J. Physiol. Lung Cell Mol. Physiol., 281, L598-606 (2001).

Gitter, et al., "Amyloid beta Peptide Potentiates Cytokine Secretion by Interleukin-1 Beta Activated Human Astrocytoma Cells", Proc. Nat. Acad. Sci. (USA), 92, 10738-10741 (1995).

Goping, et al., "MPTP Destroys a Specific Tyrosine Hydroxylase-Positive Dopaminergic Nucleus in the Goldfish Forebrain: Specific Protection by L-Deprenyl but not Clorgyline", Brain Research, 687, 35-52 (1995).

Gottlieb, et al., "Mutant Cystic Fibrosis Transmembrane Conductance Regulator Inhibits Acidification and Apoptosis in C127 Cell: Possible Relevance to Cystic Fibrosis", Proc. Nat. Acad. Sci. (USA), 93, 3587-3591 (1996).

Graever, et al., "Genomic Profiling of Drug Sensitivities Via Induced Haploinsufficiency", Nat. Genet., 3, 278-283 (1999).

Griesenbach, et al., "Anti-Inflammatory Gene Therapy Directed at the Airway Epithelium", Gene Therapy, 7: 306-313 (2000).

Griesenbach, et al., "Towards Anti-Inflammatory Lung Gene Therapy". Pediatric Pulm., S19, 237 (1999a).

Grigolo B, Roseti L, Lisignoli G, Remiddi G, Facchini A. Expression of different chemokines by human osteosarcoma cells in response to tumor necrosis factor-alpha. Anticancer Res. 19:3093-3098, 1999.

Grunblatt, et al., "Gene Expression Analysis in N-Methyl-4-Phenyl-1,2,3,6-Tetrahydropyridine Mice Model of Parkinson's Disease Using cDNA Microarray: Effect of R-Apomorphine", J. Neurochem, 78, 1, 1-12 (2001).

Guay-Broder, et al., "A-1Receptor Antagonist "Cyclopentyl-1,3-Dipropylxanthine Selectively Activates Chloride Efflux from Human Epithelial and Mouse Fibroblast Cell Lines Expressing the Cystic Fibrosis Transmembrane Regulator AF508 Mutation", Biochemistry, 34, 9079-9087 (1995).

Guo H, Tong N, Turner T, Epstein L G, McDermott M P, Kilgannon P, Gelbard H A.; Release of the neuronal glycoprotein ICAM-5 in serum after hypoxic-ischemic injury. Ann Neurol. October; 48(4):590-60 (2000).

Harada A, Sekido N, Akahoshi T, Wada T, Mukaida N and Matsushima K. *Essential involvement of interleukin-8 (IL-8) in acute inflammation. J. Leuk. Biol.* 56:559-564, 1994.

Hayashida, et al., "Synovial Stromal Cells from Rheumatoid Arthritis Patients Attract Monocytes by Producing MCP-1 and IL-8", Arthritis Res., 3, 118-126 (2001).

Hoxtermann, et al., "Fumaric Acid Esters Suppress Peripheral CD4- and CD8-Positive Lymphocytes in Psoriasis", Dermatology, 196, 223-230 (1998).

Huang S, Robinson J B, DeGuzman A, Bucana C D and Fidler I J Blockade of nuclear factor kB signaling inhibits angiogenesis and tumorigenicity of human ovarian cancer cells by suppressing expression of vascular endothelial growth factor and Interleukin-8. *Cancer Res.* 60:5334-5339, 2000

Imada, et al., "Coordinate Upregulation of Interleukin-8 and Growth-Related Gene Product-Alpha is Present in the Colonic Mucosa of Inflammatory Bowel", Scand. J. Gastroent., 36, 854-864 (2001).

Inoue, et cd., "Adenoviral-Mediated Gene Therapy of Human Bladder Cancer with Antisense Interleukin-8", Oncol. Rep., 8, 955-964 (2001).

Ionoco, et al., "Interleukin-8 Levels and Activity in Delayed-Healing Human Thermal Wounds, Wound Repair Regeneration, 8, 216-225 (2000).

Ismailov, et al., "Regulation of Epithelial Sodium Channel by the Cystic Fibrosis Transmembrane Conductance Regulator", J. Biol. Chem., 271, 4725-4732 (1996).

Ito, et cd., "Significance of Elevated Serum Interleukin-8 in Patients Resuscitated After Cardiopulmonary Arrest, Resuscitation, 51: 47-53 (2001).

Jacobson, et al., "Stimulation by Alkylxanthines of Chloride Efflux in CFPAC-1 Calls Does not Involve A, Adenosine Receptors", Biochemistry, 34, 9088-9094 (1995).

Jovov, et al., "Cystic fibrosis Transmembrane Conductance Regulator is required for Protein Kinase A Activation of an Outwardly Rectified Anion Channel Purified from Bovine Tracheal Epithelia", J, Biol. Chem., 270, 1521-1528 (1995).

Kadonaga, et al., "Affinity Purification of Sequence-Specific DNA Binding Proteins", Proc. Nat. Acad. Sci. (USA), 83, 889-893 (1986).

Karashima T, Sweeney P, Kamat A, Huang S, Kim S J, Bar-Eli M, McConkey D J and Dinney C N P Nuclear Factor kB mediates angiogenesis and metastasis of human bladder cancer through regulation of Interleukin-8. *Clin. Can. Res.* 9:2786-2797, 2003.

Kartner, et al., "Mislocalization of AF508 CFTR in Cystic Fibrosis Sweat Gland", Nature Genetics, 1, 321-327 (1992).

Kartner, et al., "Expression of the Cystic Fibrosis Gene in Non-Epithelial Invertebrate Cells Produce a Regulated Anion Conductance", Cell, 64, 681-691 (1991).

Kent, et al., "Eukaryotic Phospholipid Biosynthesis", Ann. Rev. Biochem., 64, 315-343 (1995).

Kerem, et al., "Identification of the Cystic Fibrosis Gene: Genetic Analysis", Science, 245, 1073-1080 (1998).

Kingsbury, et al., Poisonous Plants of the United States and Canada, Prentice-Hall, Inc. Englewood Cliff, N.J., 626 (1964).

Klingenhoff, et al., "Functional Promoter Modules Can Be Detected by Formal Models Independent of Overall Nucleotide Similarity", Bioinformatics, 15, 180-186 (1999).

Koch, et al., "Regulation of Angiogenesis by the C—X—C Chemokines Interleukin-8 and Epithelial Neutrophil Activating Peptide 78 in the Rheumatoid Joint", Arthritis Rheum., 44: 31-40 (2001).

Konig, et al., "Inflammatory Infiltrate and Interleukin-8 Expression in the Synovium of Psoriatic Arthritis—An Immunohistochemical and mRNA Analysis", Rheumatol. Int., 17, 159-68 (1997).

Konstan, et al., "Effect of High Dose Ibuprofen in Patients with Cystic Fibrosis", New Eng. J. Med, 332, 848-854 [and comments in same journal: 332: 886-887; 333:

Kortekaas, R., Leenders, K. L., Van Oostrom, J. C., Vaalburg, W., Bart, J., Willemsen, A. T., Hendrikse, N. H., 2005. Blood-brain barrier dysfunction in parkinsonian midbrain in vivo, Ann. Neurol. 57, 176-179

Kossman, et al., "Interleukin-8 Released Into Cerebrospinal Fluid After Brain Injury is Associated with Blood-Brain Barrier Dysfunction and Nerve Growth Factor Production, J. Cerebr. Blood Flow Metab., 17, 280-289 (1997).

Kostulas, et al., "Increased IL-1beta, IL-8 and IL-17 mRNA Expression in Blood Mononuclear Cells Observed in a Prospectiveischemic Stroke Study, Stroke, 30, 2174-2179 (1999).

Kraan, et al., "The Development of Clinical Signs of Rheumatoid Synovial Inflammation is Associated with Increased Synthesis of the Chemokine CXCL8 (interleukin-8)", Arthritis Res, 3: 65-71 (2001).

Keuter et al., Patterns of cytokines and inhibitors during typhoid fever. J, Inf. Dis. 169:1306-1311 (1994).

Kruger, et al., "Genetic Analysis of Immunomodulating Factors in Sporadic Parkinson's Disease", J. Neural. Trans., 2000; 107, 553-562 (2000).

Kulikov A, Eva A, Kirch U, Boldyrev A, Scheiner-Bobis G. Ouabain activates signaling pathways associated with cell death in human neuroblastoma. Biochim. Biophys. Acta 1768: 1691-1702, 2007.

Kurzrock R, "Cytokine regulation in cancer." *Biomed. Pharmacother.* 55:543-547, 2001.

Kutsch, et al., "Induction of the Chemokines Interleukin-8 and IP-10 by Human Immunodeficiency Virus Type 1 tat in astrocytes", J. Virol., 74, 9214-9221 (2000).

Laffon, et al., "Interleukin-8 Mediates Injury from Smoke Inhalation to Both the Lung Epithelial and Alveolar Epithelial Barriers in Rabbits", Am. J. Respir. Crit. Care Med., 160, 1443-1449 (1999).

Lamprecht, et al., "The Role of NHERF and E3KARP in the cAMP-Mediated Inhibition of NHE3, J. Biol. Chem., 273, 29972-29978 (1998).

Landi S, Moreno V, Giola-Patrociola L, Guino E, Navarrp M, de Ora J, Capella G, and Canzian F (for the Bellvitge Colorectal Cancer Study Group) *Cancer Research* 63: 3560-3566, 2003.

Lauren et al, Transcriptome analysis of the hippocampal CA1 pyramidal cell region after kainic acid-induced status epilepticus in juvenile rats. *PLoS One.* 2010 5(5): e10733. doi: 10.1371/journal.pone.0010733.PMID: 20505763,2010

Lekstrom-Himes J A, Kuhns D B, Alvord W G and Gallin J I Inhibition of human neutrophil IL-8 production by hydrogen peroxide and dysregulation in chronic granulomatous disease *J. Immunol.* 174: 411-417, 2005

Lekstrom-Himes J A and Gallin J I Immunodeficiency diseases caused by defects in phagocytes *N. Eng. J. Med.* 343: 1703-1714, 2000.

Lev D C, Ruiz M, Mills L, McGary E C, Price J E and Bar-Eli M Decarbazine causes transcriptional up-regulation of Interleukin 8 and vascular endothelial growth factor in melanoma cells: a possible escape mechanism from chemotherapy. *Mol. Cancer. Therap.* 2: 753-763, 2003.

Link, et al., "Direct Analysis of Protein Complexes Using Mass Spectroscopy, Nature Biotechnology, 17, 676-682 (1999).

Lipsky, et al., "Rheumatoid Arthritis", Harrisons Principles of Internal Medicine, 15th edition (eds, Braunwald, et al.) McGraw-Hill, Pubs., New York, 1929-1937 (2001).

Lu X Y, Zhu C Q, Qian J, Chen X X, Ye S, Gu Y Y. Intrathecal cytokine and chemokine profiling in neuropsychiatric lupus or lupus complicated with central nervous system infection. *Lupus.* 19:689-695, 2010.

Lukacs, et al., "Conformational Maturation of CFTR but not Its Mutant Counterpart (AF508) Occurs in the Endoplasmic Reticulum and Requires ATP", EMBO J., 13, 60766086 (1994).

Lun M, Zhang P L, Pelliteri P K, Law A, Kennedy T L, and Brown R E Nuclear factor-kappa B pathway as a therapeutic target in head and neck squamous cell carcinoma: pharmaceutical and molecular validation using velcade and si-RNA/NFkB. *Ann. Clin. Lab. Sci.,* 35:251-258, 2005

Maier, et al., "Differential Release of Interleukines 6, 8, and 10 in Cerebrospinal Fluid and Plasma After Traumatic Brain Injury", Shock, 15, 421-426 (2001).

Malech H L and Hickstein D D. Genetics, biology and clinical management of myeloid cell primary immune deficiencies: chronic granulomatous disease and leukocyte adhesion deficiency *Curr. Opinion Hematol.* 14:29-36, 2007.

Mandel, et al., "cDNA Microarray to Study Gene Expression of Dopaminergic Neurodegeneration and Neuroprotection in MPTP and 6-Hydroxydopamine Models: Implications for Idiopathic Parkinson's Disease", J. Neural Transm. Suppl., 117-124 (2000).

Manna, et al., "Oleandrin Suppresses Activation of Nuclear Transcription Factor-kB, Activator Protein-1 and c-Jun NH2-Terminal Kinase, Cancer Research, 60, 3838-3847 (2000).

Marguet, et al., "Eosiniophilcation Protein and Interleukin-8 Levels in Bronchial Lavage Fluid from Children with Asthma and Infantile Wheeze", Pediatr. Allergy Immunol., 12, 27-33 (2001).

Masters S L, Simon A, Aksentijevich I, Kastner D L Horror autoinflammaticus: The molecular pathophysiology of autoinflammatory disease. *Ann. Rev. Immunol.* 27: 621-668, 2009.

Matsumoto, et al., "Pivotal Role of Interleukin-8 in the Acute Respiratory Distress Syndrome and Cerebral Reperfusion Injury", J. Leukoc. Biol., 62, 581-587 (1997a).

Matsumoto, et al., "Prevention of Cerebral Edema and Infarct in Cerebral Reperfusion Injury by an Antibody tolinterleukin-8", Lab Invest., 77, 119-125 (1997b).

Modelska, et al., "Acid-Induced Lung Injury. Protective Effect of Anti-Interleukin-8 Pretreatment on Alveolar Epithelial Barrier Function in Rabbits", Am. J. Respir. Crit. Care Med., 160, 1441-1442 (1999).

Merritt W M, Lin Y G, Spannuth W A, Fletcher M S, Kamat A A, Han L Y, Landen C N, Jennings N, De Geest K, Langley R R, Villares G, Sanguino A, Lutgendorf S K, Lopez-Berestein G, Bar-Eli M M, Sood A K. Effect of interleukin-8 gene silencing with liposome-encapsulated small interfering RNA on ovarian cancer cell growth. J Natl Cancer Inst. 2008 Mar. 5; 100(5):359-72. Epub 2008 Feb. 26.

Mian B M, Dinney C N P, Bermajo C E, Sweeney P, Tellez C, Yang X D D, Gudas J M, McConkey D J and Bar-Eli M Fully human anti-Interleukin 8 antibody inhibits tumor growth in orthotopic bladder cancer xenografts via down regulation of matrix metalloproteases and Nuclear Factor-KB. *Clin. Can. Res.* 9:3167-3175, 2003

Millar H J, Nemeth J A, McCabe F L, Pikounis B, and Wickstrom E, Circulating human interleukin-8 as an indicator of cancer progression in a nude rat orthotopic human non-small cell lung carcinoma model. *Cancer Epidemiol. Biomark. Prev.* 17:2180-2187, 2008.

Morel, et al., "Interleukin-18 Induces Rheumatoid Arthritis Synovial Fibroblast CXC Chemokine Production Through NFkappaB Activation", Lab Invest, 81, 1371-1383 (2001).

Moscova M, Marsh D J and Baxter R C Protein chip discovery of secreted proteins regulated by the phosphatidylinositol-3 kinase pathway in ovarian cancer cell lines. *Cancer Research* 66:1376-1383, 2006.

Moyer, et al., "A PDZ Interacting Domain in CFTR is Required for Apical Polarization and Export from the Endoplasmic Reticulum", Pediatric Pulm, S19, 164 (1999a).

Moyer, et al., "PDZ Interacting Domain in CFTR is an Apical Membrane Polarization Signal", J. Clin. Inv., 104, 1353-1361 (1999b).

Muehlstedt, et al., "Cytokines and Pathogenesis of Nosocomial Pneumonia", Surgery, 130, 602-609 (2001).

Mukaida, et al, "Inhibition of Neutrophil-Mediated Acute Inflammation Injury by an Antibody Against Interleukin-8 (IL-8), Inflamm. Res. Suppl., 3, S 151-157 (1998).

Murayama, et al., "The Immediate Early Gene 1 Product of Human Cytomegalovirus is Sufficient for Upregulation of Interleukin-8 Gene Expression", Biochem. Biophys. Res. Comm., 279, 298-304 (2000).

Nandate, et al., "Cerebrovascular Cytokine Response During Coronary Artery Bypass Surgery: Specific Production of Interleukin-8 and its Attenuation by Hypothermic Cardiopulmonary Bypass", Anesth. Analg., 89, 823-828 (1999).

Nakamura, et al., Am. J. Respir. Crit. Care Med., 161, 1030-1036 (2000).

Nanki, et al., "Chemokines Regulate IL-6 and IL-8 Production by Fibroblast-Like Synoviocytes from Patients with Rheumatoid Arthritis", J Immunol., 167, 5381-5385 (2001).

Naren, A. P., Nelson, D. J., Xie, W., Jovov, B., Pevsner, J., Bennett, M. K., Benos, D. J., Quick, M. W., and Kirk, K. L. Regulation of CFTR chloride channels by syntaxin and Munc18 isoforms. Nature 390: 302-305 (1997).

Naren, A. P., Quick, M. W., Collawn, J. G., Nelson, D. J., and Kirk, K. L. Syntaxin 1A inhibits CFTR chloride channels by means of domain-specific protein-protein interactions. Proc. Nat. Acad. Sci. (USA ! 95: 10972-10977 (1998).

Nishimura, et al., "Tumor Necrosis Factor Gene Polymorphisms in Patients with Sporadic Parkinson's Disease", Neurosci. Lett., 311, 1-4 (2001).

Notarnicola C, Didelot M N, Demaille J, Toutitou I Enhanced cytokine mRNA levels in attack-free patients with familial mediterranean fever. *Genes and Immunity* 3: 43-45, 2002

Nourbaksh, et al., "The NF-KappaB Repressing Factor NRF is Involved in Basal Repression and Interleukin (IL)-1-Induced Activation of IL-8 Transcription by Binding to a Conserved NF-KappaB-Flanking Sequence Element", J. Biol. Chem., 44, 4501-4508 (2000).

Ohata Y, Harada T, Miyakoda H, Taniguchi F, Iwabe T, Terakawa N. Serum interleukin8 levels are elevated in patients with ovarian endometrioma. *Fertil. Steril.* 90:994-999, 2008

Olszewski, et al., "Lymph Draining from Foot Joints in Rheumatoid Arthritis Provides Insight into Local Cytokine and Chemokine Production and Transport to Lymph Nodes", Arthritis Rheum., 44, 541-549 (2001).

Osman, et al., "A Monoclonal Anti-Interleukin-8 Antibody (WS-4) Inhibits Cytokine Response and Acute Lung Injury in Experimental Severe Acute Necrotising Pancreatitis in Rabbits", Gut, 43, 232-239 (1988).

Osman, et al., "Graded Experimental Acute Pancreatitis: Monitoring of a Renewed Rabbit Model Focusing on the Production of Interleukin-8 (IL-8) and CD 1b/CD 18", Eur. J. Gastroenterol. Hepatol., 11, 137-149 (1999).

Ott, et al., "Cytokines and Metabolic Dysfunction after Severe Head Injury", J. Neurotrauma, 11, 447-472 (1994).

Pearson, et al., "Structure of the ERM Protein Moesin Reveals the FERM Domain Fold Masked by an Extended Actin Binding Tail Domain", Cell, 101, 259-270 (2000).

Pier, et al., "Role of Mutant CFTR in Hypersusceptibility of Cystic Fibrosis Patients to Lung Infections", Science, 271, 64-67 (1996).

Pilewski, et al., "Role of CFTR in Airway Disease", Physiol. Rev., 79, S215-S255 (1999).

Ping Y and Yao X Inhibition of functional chemokine receptor CXCR4 reduces the production of IL-8 and VEGF by malignant human glioma cells. *AACR Meeting Abstracts* A109, 2006.

Pollard et al, "The TARC/sICAM5 Ratio in Patient Plasma is a Candidate Biomarker for Drug Resistant Epilepsy". *Front Neurol.;* 3:181. doi: 10.3389/fneur.2012.00181, 2013

Pollard, et al., "A Parkinsonian Syndrome Induced in the Goldfish by the Neurotoxin MPTP", FASEB J., 6, 3108-3116 (1992).

Pollard, et al., "Anatomical Genomics: Systems of Genes Underlying the Biology of Systems", Anatomical Rec., 259: iii-ix (2000).

Pollard, et al., "Role of CPX in Promoting Trafficking and Chloride Channel Activity of Wildtype and Mutant CFTR", Pediatric Pulmonology, S14, 128-131 (1997).

Preston, M. J., et al., "Rapid and Sensitive Method for Evaluating *Pseudomonas Aeruginosa* Virulence Factors During Corneal Infections in Mice", Infect. Immun., 63, 3497-3501 (1995).

Qiu J, Gao H-Q, Li B-Y, Shen L Proteomics investigation of protein expression changes in ouabain induced apoptosis in human umbilical vein endothelial cells. *J. Cellular Biochem,* 104:1054-1064, 2008a Qiu J, Gao H-Q, Liang Y, Yu H, and Zhou R-H Comparative proteomics analysis reveals role of heat shock protein 60 in digoxin-induced toxicity in human endothelial cells. *Biochim. Biophys. Acta* 1784: 1857-1864, 2008b.

Raghuram, V., et al., "Multiple PDZ Domains Involved in the Association of NHERF with CFTR", Pediatric Pulm., S19, 178 (1992).

Rahman Attu, Harvey K, Siddiqui R A. Interleukin-8: An autocrine Inflammatory Mediator. Current Pharmaceutical Design 5:241-253, 1999.

Richman-Eisenstat, et al., "Interleukin-8: an Important Chemoattractant in Sputum of Patients with Chronic Inflammatory Airway Diseases", Am. J. Physiol., 264, L413-418 9 (1993).

Riordan, et al., "Identification of the Cystic Fibrosis Gene: Cloning and Characterization of Complementary DNA", Science, 245, 1066-1073 (1989).

Rodenburg, et al., "Superinduction of Interleukin 8 mRNA in Activated Monocyte Derived Macrophages from Rheumatoid Arthritis Patients", Ann. Rheum. Dis., 58.64852 (1999).

Rodriguez, et al., "Correlation of the Local and Systemic Cytokine Response with Clinical Outcome Following Thermal Injury", J. Trauma, 34, 684-694 (1993).

Roebuck, et al., "Regulation of Interleukin-8 Gene Expression, J. Interferon Cytokine Res., 19, 429-438 (1999).

Rommens, et al., "Identification of the Cystic Fibrosis Gene: Chromosome Walking and Jumping", Science, 245, 1, 1059-1065 (1989).

Rosenfeld, M. and Ramsey, B. Evolution of airway microbiology in the infant with cystic fibrosis: role of nonpseudomonal and pseudomonal pathogens. *Semin. Respir. Infect.* 7: 158-167 (1992).

Rothe, et al., "Human Osteoclasts and Osteoclast-Like Cells Synthesize and Release High Basal and Inflammatory Stimulated Levels of the Potent Chemokine Interleukin-8", Endocrinology, 139, 4353-4363 (1998).

Rottman, J. B. Key Role of Chemokines and Chemokine Receptors in Inflammation, Immunity, Neoplasia, and Infectious Disease, Vet Pathol 36:357-367 (1999).

Ruef, et al., "Regulation of Cytokine Secretion by Cystic Fibrosis Airway Epithelial Cells", Eur. Resp. J., 6, 1429-1436 (1993).

Rutkowski P, Kaminska J, Kowalska M, Ruka W, Steffen J. Cytokine and cytokine receptor serum levels in adult bone sarcoma patients: correlations with local tumor extent and prognosis. J Surg Oncol. 84:151-159, 2003

Salcedo R, Martinas-Green M, Gertz B, Oppenheim J J, and Murphy W J Combined administration of antibodies to human interleukin-8 and epidermal growth factor receptor results in increased antimetastatic effects on human breast cancer carcinoma xenografts. *Clin. Cancer Res.* 8:2655-2665, 2002.

Schultz, et al., "Pharmacology of CFTR Chloride Channel Activity", Physiol. Rev., 79, 5109-5144 (1999).

Schultz, et al., "IBMX Stabilizes the ATP-Bound State of AF508-CFTR", J. Gen. Physiol., 104, 35a (1994).

Schwiebert, et al., "Chemokine expression in CF Epithelia: Implications for the Role of CFTR in RANTES Expression", Am. J. Physiol., 276, C700-710 (1999).

Shak, et al., "Recombinant Human DNAsel I Reduces Viscosity of Cystic Fibrosis Sputum", Proc. Nat. Acad. Sci. (USA), 87, 9188-9192 (1990).

Sherwood, et al., Interleukin-8, Neuroinflammation, and Secondary Brain Injury", Crit. Care Med, 28, 1221-1223 (2000).

Shirayoshi, et al., "Binding of Multiple Nuclear Factors to the 5'Upstream Regulatory Element of the Murine Major Histocompatibility Class I Gene", Mol. Cell Biol., 7, 4542-4548 (1987).

Short, et al., "An Apical PDZ Protein Anchors the Cystic Fibrosis Transmembrane Conductance Regulator to the Cytoskeleton", J. Biol. Chem. 273, 19797-19801 (1998).

Silvestroni A, Faull R L, Strand A Q D and Moller T. Distinct neuroinflammatory profile in post-mortem human Huntington's disease. *Neuroreport* 20: 1098-1103, 2009.

Skov L, Beurskens F J, Zachariae C O C, Reitamo S, Teeling J, Satijn D, Knudsen K M, Boot E P J, Hudson D, Baadsgaard 0, Parren P W H I, and Winkel J G J. IL-8 as antibody therapeutic target in inflammatory diseases: Reduction of clinical activity in palmoplantar pustulosis. *J. Immunol.* 181:669-679, 2008.

Srivastava, et al., "Low in vivo Levels of Human Anx7 (Annexin VII) Gene Expression are Due to Endogenous Inhibitory Promoter Sequences", Cell Biology Internat., 24, 475481 (2000).

Srivastava, et al., "Pharmacogenomics of the Cystic Fibrosis Transmembrane Conductance Regulator (CFTR) and the Cystic Fibrosis Drug CPX Using Genome Microarray Analysis", Molecular Med., 5, 753-767 (1999).

Srivastava, et al., "Digitoxin mimics gene therapy with CFTR and suppresses hypersecretion of IL-8 from systic fibrosis lung epithelial cells". Proc Natl Acad. Sci (USA) 101:7693-7698, (2004).

Stangl, et al., "Influence of Brain Death on Cytokine Release in Organ Donors and Renal Transplants". Transplant. Proc., 33, 1284-1285 (2001).

Straczkowski, Marek, Irina Kowalska, Agnieszka Nikolajuk, Stella Dzienis-Straczkowska, Malgorzata Szelachowska and Ida Kinalska. Plasma interleukin 8 concentrations in obese subjects with impaired glucose tolerance. *Cardiovascular Diabetology* 2003, 2:5

Stein, et al., "Distinct Mechanisms for Regulation of the Interleukin-8 Gene Involve Synergism and Cooperativity Between C/EBP and NF-Kappa B., Mol. Cell Biol., 13, 7191-7198 (1993).

Stoof, et al., "The Antipsoriatic Drug Dimethylfumarate Strongly Suppresses Chemokine Production in Human Karatinocytes and Peripheral Blood Mononuclear Cells", Br. J. Dermatol. 144: 1114-1120 (2001).

Stuffs, et al., "CFTR as a cAMP-Dependent Regulator of Sodium Channels", Science, 269, 847-850 (1995).

Subauste, et al., "Effects of Tumor Necrosis Factor Alpha, Epidermal Growth Factor and Transforming Growth Factor Alpha on Interleukin-8 Production by, and Human Rhinovirus Replication in, Bronchial Epithelial Cells", Int. Immunopharmacol., 1, 12291234 (2001).

Sun, et al., "The PDZ Domain-Containing Protein E3KARP Couples EZRIN to Cystic Fibrosis Transmembrane Conductance Regulator (CFTR)", Pediatric Pulm., S 19, 164 (1994).

Suzuki, et al., "Tax protein of FITLV-1 Interacts with the Rel Homology Domain of NFKB p65 and c-Rel Proteins Bound to the NFKB Binding Site and Activates Transcription, Oncogene, 9, 3099-3105 (1994).

Tabary, et al., "Selective Upregulation of the Chemokine IL-8 Expression in Cystic Fibrosis Bronchial Gland Cells in vivo and in vitro", Am. J. Path., 153, 921-930 (1998).

Takahashi, et al., "The Participation of IL-8 in the Synovial Lesions at an Early Stage of Rheumatoid Arthritis", Tohoku J Exp Med., 188, 75-87 (1998).

Takata, et al., "Prevastatin Suppresses Interleukin-8 Production Induced by Thrombin in Human Aortic Endothelial Cells Cultures with High Glucose by Inhibiting the p44/42 Mitogen Activated Protein Kinase", Br. J. Pharm., 134, 753-762 (2001).

Tanaka, et al., "Medium-Chain Fatty Acids Stimulate Interleukin-8 Production in Caco-2 Cells with Different Mechanisms from Long Chain Fatty Acids: J. Gastroent. Hepatol., 16, 748-754 (2001).

Tansey et al Neuroinflammation in Parkinson disease: potential environmental triggers, pathways and targets for early therapeutic intervention. Exptl. Neurol. 208:1-25, 2008

Tarkowski, et al., "Intrathecal Release of Pro- and Anti-Inflammatory Cytokines During Stroke", Clin. Exp. Immunol., 110, 492-499 (1997).

Temaru, et al., "High Glucose Enhances the Gene Expression of Interleukin-8 in Human Endothelial Cells, but not Smooth Muscle Cells: Possible Role of Interleukin-8 in Diabetic Macroangiopathy", Diabetologia, 40, 610-613 (1997).

Troughton, et al., "Synovial Fluid Interleukin-8 and Neutrophil Function in Rheumatoid Arthritis and Seronegative Polyarthritis", Br. J. Rheumatol., 35, 1244-1251 (1996).

Tsui, et al., "Mutations and Sequence Variations Detected in the Cystic Fibrosis Transmembrane Conductance Regulator (CFTR) Gene: A Report from the Cystic Fibrosis Genetic Analysis Consortium", Hum. Mut., 1, 197-203 (1992a).

Tsui, et al., "The Spectrum of Cystic Fibrosis Mutations", Trends in Genetics, 8, 392-398 (1992b).

Ulukus M, Ulukus E C, Tavmergen-Goker E N, Tavmergen E, Zheng E, and Arici A. Expression of IL-8 and monocyte chemotactic protein 1 in women with endometriosis *Fertil. Steril.* 91:687-693, 2009

Vandermeeren, et al., "Dimethylfumarate is an Inhibitor of Cytokine-Induced Nuclear Translocation of NFKB 1, but Not ReIA in Normal Human Dermal Fibroblast Cells", J. Invest. Dermatol., 116, 124-130 (2001).

Victor, et al., "CCAAT Box Enhancer Protein Alpha (C/EBP-alpha) Stimulates KappaB Element-Mediated Transcription in Transfected Cells", J. Biol. Chem., 271, 5595-5602 (1996).

Vindenes, et al., "Increased Levels of Circulating Interleukin-8 in Patients with Large Burns: Relation to Burn Size and Sepsis", J. Trauma, 39, 635-640 (1995).

Wang, N., et al., Interleukin-8 is Induced by Cholesterol Loading of Macrophages and Expressed by Macrophage Foam Cells in Human Atheroma", J. Biol. Chem., 271, 88378842 (1996).

Ward, et al., "Degradation of CFTR by the Ubiquitin-Proteosome Pathway. Cell, 83, 121127 (1995).

Ward, et al., "Intracellular Turnover of Cystic Fibrosis Transmembrane Conductance Regulator. Inefficient Processing and Rapid Degradation of Wildtype and Mutant Protein, J. Biol. Chem., 269, 25710-25718 (1994). I Welsh, et al., "Cystic Fibrosis", The Metabolic and Molecular Bases of Inherited Diseases, Scriver, et al., eds.), 7'sedition, 3799-3876, McGraw-Hill, New York (1995).

Whalen, et al., "Interleukin-8 is Increased in Cerebrospinal Fluid of Children with Severe Head Injury", Crit. Care Med., 28, 1221-1234 (2000).

Whitton, P. S., 2007 Inflammation as a causative factor in the aetiology of Parkinson's disease, Br. J. Pharmacol. 50, 963-976

Wu, et al., "CCAAT/Enhancer-Binding Protein (C/EBP) Bind to Overlapping Elements Within the Interleukin-8 Promoter. The role of Oct. 1 as a Transcriptional Repressor", J. Biol. Chem., 272, 2396-2403 (1997).

Xia, et aL, "Interleukin-8 Receptor Immunoreactivity in Brain and Neuritic Plaques of Alzheimer's Disease", Am. J. Path., 150, 1267-1274 (1997).

Yang, et al., "The Common Variant of Cystic Fibrosis Transmembrane Conductance Regulator is Recognised by Hsp70 and Degraded in a Pre-Golgi Non-Lysosomal Compartment", Proc. Nat. Acad. Sci. (USA), 90, 9480-9484 (1993).

Yang, et al. "Cardiac Glycosides inhibit TNS-alpha/NF-kappaB signaling by blocking recruitment of TNF receptor-associated death domain to the TNF receptor", Proc Nat Acad Sci (USA), 102:9631-9636 (2005)

Yeh, et al., "Changes in Levels of IL-8 in Burned Patients", Burns, 23, 555-559 (1997).

Yoshida, et al, "Inhibition of IL-6 and IL-8 Induction From Cultured Rheumatoid Synovial Fibroblasts by Treatment with Aurothioglucose", Int. Immunol., 11, 151-158 (1997).

Youn et al, "Serial examination of serum IL-8, IL-10 and IL-1Ra levels is significant in neonatal seizures induced by hypoxic-ischaemic encephalopathy". Scand J Immunol. 76(3):286-93. doi: 10.1111/j.1365-3083.2012.02710. PMID:22537067, 2012

Yuuki, et al., "Inflammatory Cytokines in Vitreous Fluid and Serum of Patients with Diabetic Retinopathy", J. Diabetes Complications, 15, 257-259 (2001).

Zampronio, et al., "Interleukin-8 Induces Fever by a Prostaglandin-Independent Mechanism", Am. J. Physiol., 266, R1670-1674 (1994).

Zhang et al. CSFD multianalyte profile distinguishes Alzheimer Disease and Parkinson Disease. Am. J. Clin. Path. 129:526-529, 2008.

Zheng, S., De, B. P., Choudhary, S., Comhair, S. A. A., Goggans, T., Slee, R., Williams, B. R. G., Pilewski, J., Hague, S. H., and Erzurum, S. C. Impaired innate host defense causes susceptibility to respiratory virus infections in cystic fibrosis. Immunity 18:619-630 (2003).

Zeitlin, et al., "A Cystic Fibrosis Bronchial Epithelial Cell Line: Immortalization by Adeno12-SV40 Infection", Am. J. Respir. Cell Mol. Biol., 4, 313-319 (1991).

Zhang, et al., "CPX Affects Expression and Trafficking of AF508-CFTR. Pediatric Pulm., S 19, 182 (1999).

Zhu Y M, Webster S J, Flower D and Woll P J Interleukin 8/CXCL8 is a growth factor for human lung cancer cells Brit. J. Cancer 91:1970-1976, 2004.

Zivna, et al., The Role of Cytokines and Antioxidant Status in Graft Quality Prediction", Transpl. Proc., 31, 2094 (1999).

Zozulinska, et al., Serum Interleukin-8 Level is Increased in Diabetic Patients", Diabetologia, 42, 117-118 (1998).

What is claimed is:

1. A method of decreasing or inhibiting inflammation in a mammal suffering from a disease condition caused or aggravated by an excessive level of proinflammatory mediator IL-8, IL-6, or IL-8 and IL-6, comprising administering a cardiac glycoside at a concentration of from about 1 nM to about 2 nM,
wherein the cardiac glycoside is digitoxin, and
wherein the disease condition is castration resistant prostate cancer.

2. A method of inhibiting the growth and metastases of castration-resistant prostate cancer comprising:
administering to a recipient in need of treatment a cardiac glycoside at a concentration of from about 1 nM to about 2 nM to suppress a proinflammatory mediator including digitoxin-dependent suppression of IL-8, IL-6, or IL-8 and IL-6,
wherein the cardiac glycoside is digitoxin.

3. The method according to claim 1, wherein the digitoxin reduces serum IL-8 and IL-6 expression in castration-resistant prostate cancer.

4. The method according to claim 2, wherein the digitoxin decreases growth of a primary tumor in vivo and metastases of castration-resistant prostate cancer.

5. The method according to claim 2, wherein the digitoxin decreases number, size, and weight of metastases in castration resistant prostate cancer.

6. The method according to claim 2, wherein the digitoxin inhibits expression of messenger RNAs (mRNAs) in castration resistant prostate cancer.

7. The method according to claim 2, wherein the digitoxin enhances expression of messenger RNAs (mRNAs) in castration-resistant prostate cancer.

8. The method according to claim 6, wherein the digitoxin elevates or inhibits expression of mRNA expressed proteins whose increase is associated with increased epithelial-mesenchymal-transition (EMT) in castration resistant prostate cancer.

9. The method according to claim 2, wherein the digitoxin elevates or inhibits expression of microRNA expressed proteins needing elevation or needing reduction associated with a reduction of epithelial-mesenchymal-transition (EMT) in castration resistant prostate cancer.

10. The method according to claim 9, wherein the digitoxin elevates expression of microRNA expressed proteins needing elevation associated with a reduction of epithelial-mesenchymal-transition (EMT) in castration resistant prostate cancer.

11. The method according to claim 9, wherein the digitoxin inhibits expression of microRNA expressed metastases needing inhibition associated with a reduction of epithelial-mesenchymal-transition (EMT) in castration-resistant prostate cancer.

12. The method according to claim 9, wherein the microRNAs are selected from the group consisting of miR-122, miR-291a-3p, miR-380-3p, miR-411, miR-667, miR-670, miR-879, miR-347, miR-376a, and miR-467b.

13. The method according to claim 2, wherein the digitoxin inhibits expression of epithelial-mesenchymal-transition (EMT) associated proteins in PAIII cultures of castration resistant prostate cancer cells.

14. The method according to claim 2, wherein the digitoxin inhibits expression of proteins associated with epithelial-mesenchymal-transition (EMT) in PC3 castration resistant prostate cancer cell cultures.

15. The method according to claim 9, wherein the microRNAs from a bodily fluid are used as biomarkers for castration resistant prostate cancer.

16. The method according to claim 6, wherein the digitoxin inhibits expression of epithelial-mesenchymal-transition (EMT) messenger RNA (mRNA) genes in tumors resected from castration resistant prostate cancer.

* * * * *